(12) United States Patent
Grunstein

(10) Patent No.: US 8,569,229 B2
(45) Date of Patent: Oct. 29, 2013

(54) COMPOSITIONS AND METHODS WHICH MODULATE G-PROTEIN SIGNALING FOR THE TREATMENT OF INFLAMMATORY DISORDERS SUCH AS ASTHMA AND ALLERGIC CONJUNCTIVITIS

(75) Inventor: Michael M. Grunstein, Merion Station, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 249 days.

(21) Appl. No.: 12/852,711

(22) Filed: Aug. 9, 2010

(65) Prior Publication Data

US 2011/0008269 A1  Jan. 13, 2011

Related U.S. Application Data

(63) Continuation-in-part of application No. PCT/US2009/033581, filed on Feb. 9, 2009.

(60) Provisional application No. 61/026,915, filed on Feb. 7, 2008, provisional application No. 61/334,409, filed on May 13, 2010.

(51) Int. Cl.
*A61K 38/00* (2006.01)
*A61P 11/06* (2006.01)
*A61P 11/08* (2006.01)
*C07K 14/72* (2006.01)
*A61K 9/12* (2006.01)

(52) U.S. Cl.
USPC ............ 514/1.7; 514/20.6; 514/21.3; 424/45; 930/10; 930/300; 530/324

(58) Field of Classification Search
None
See application file for complete search history.

(56) References Cited

U.S. PATENT DOCUMENTS

| | | | |
|---|---|---|---|
| 5,250,293 | A | 10/1993 | Gleich |
| 6,017,763 | A | 1/2000 | Stephens et al. |
| 6,812,339 | B1 | 11/2004 | Venter et al. |
| 2003/0182669 | A1* | 9/2003 | Rockman et al. ............... 800/18 |
| 2006/0115813 | A1 | 6/2006 | Yang et al. |
| 2010/0130505 | A1* | 5/2010 | Smrcka et al. ............... 514/250 |

FOREIGN PATENT DOCUMENTS

| | | |
|---|---|---|
| EP | 0 896 965 | 2/1999 |
| WO | 97/49818 | 12/1997 |
| WO | 01/11933 | 2/2001 |
| WO | WO 2005063732 A1 * | 7/2005 |

OTHER PUBLICATIONS

"chronic", The American Heritage Dictionary of the English Language, Houghton Mifflin, 2007. Credo Reference. Dec. 12, 2007. Web. Dec. 19, 2012. http://www.credoreference.com/entry/hmdictenglang/chronic.*
Huang et al., Pubmed Abstract #15634388 of Zhonghua Jie He He Hu Xi Za Zhi, 27(11): 756-9 (2004).*
Ito et al., Journal of Pharmacology and Experimental Therapeutics, 321: 1-8 (2007).*
Orr et al., Journal of Biological Chemistry, 277: 20453-20460 (2002).*
Talaia et al., Neurochemistry 47: 418-429 (2005).*
Chang, M.S.S., et al. "Dissecting Intracellular Signaling Pathways with Membrane-Permeable Peptides." Sci STKE. Aug. 29, 2000;2000(47):pl1.

* cited by examiner

*Primary Examiner* — Kortney L Klinkel
*Assistant Examiner* — Lisbeth C Robinson
(74) *Attorney, Agent, or Firm* — Dann, Dorfman, Herrell & Skillman; Kathleen D. Rigaut

(57) ABSTRACT

Compositions and methods for the treatment of asthma and inflammatory ocular disorders are disclosed.

8 Claims, 25 Drawing Sheets

Figure 4
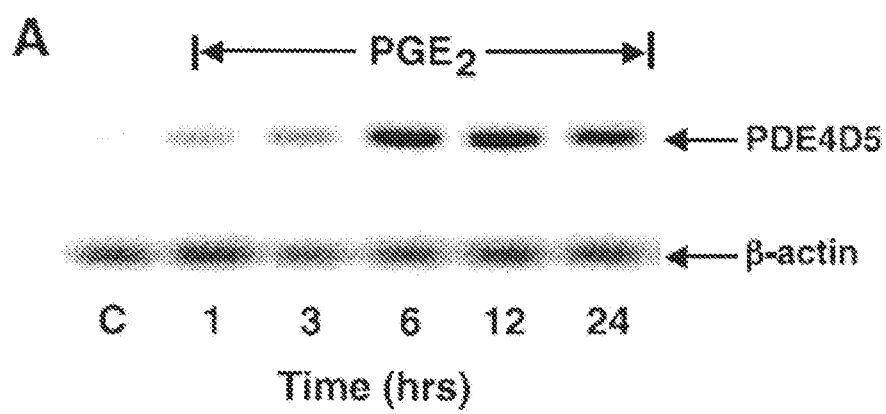
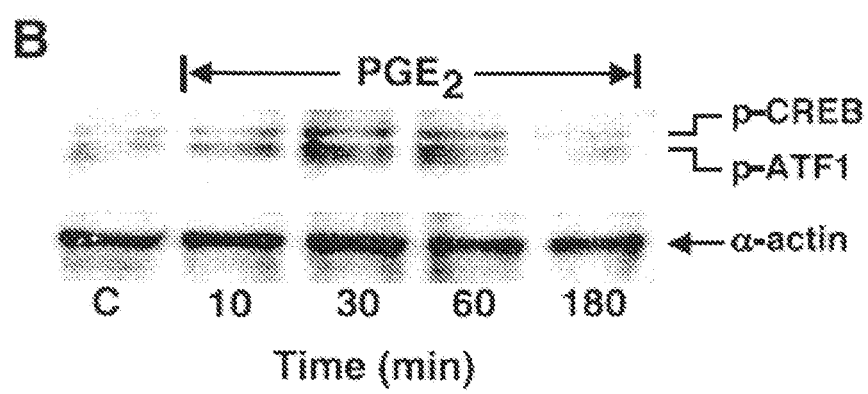
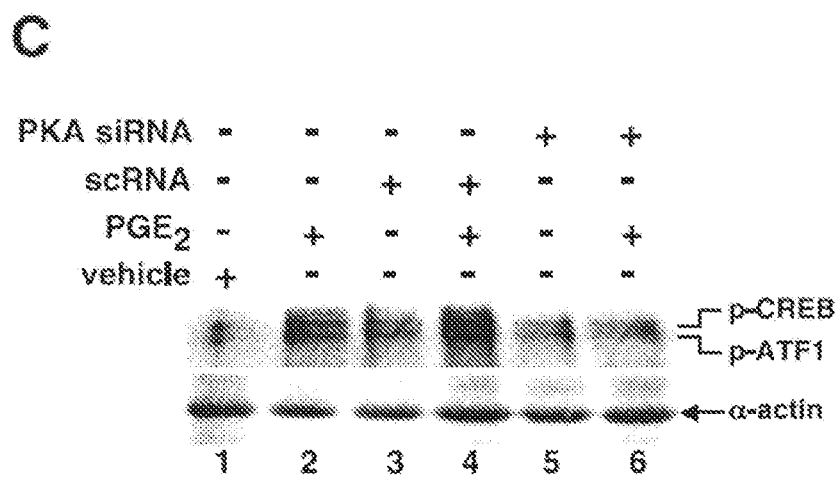

Figure 7
A
| GGTI-298 | − | − | − | − | + |
| GW5074 | − | − | − | + | − |
| U0126 | − | − | + | − | − |
| PGE$_2$ | − | + | + | + | + |
 ← p-ERK1/2
 ← α-actin
1    2    3    4    5
B
| adeno-βARK-ct | − | − | + | + |
| adeno-LacZ | + | + | − | − |
| PGE$_2$ | − | + | − | + |
 ← p-ERK1/2
 ← α-actin
1    2    3    4

SEQUENCE LISTING

<160> NUMBER OF SEQ ID NOS: 7

<210> SEQ ID NO 1
<211> LENGTH: 43
<212> TYPE: PRT
<213> ORGANISM: Artificial Sequence
<220> FEATURE:
<223> OTHER INFORMATION: Synthetic Sequence

<400> SEQUENCE: 1

Ala Ala Val Ala Leu Leu Pro Ala Val Leu Leu Ala Leu Leu Ala Val
1               5                   10                  15

Thr Asp Gln Leu Gly Glu Asp Phe Phe Ala Val Asp Leu Glu Ala Phe
            20                  25                  30

Leu Gln Glu Phe Gly Leu Leu Pro Glu Lys Glu
        35                  40

<210> SEQ ID NO 2
<211> LENGTH: 22
<212> TYPE: DNA
<213> ORGANISM: Artificial Sequence
<220> FEATURE:
<223> OTHER INFORMATION: Primer

<400> SEQUENCE: 2
tgccagctgt acaaagttga cc                                                22

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
ttctcggaga gatcactgga ga                                                22

<210> SEQ ID NO 4
<211> LENGTH: 24
<212> TYPE: DNA
<213> ORGANISM: Artificial Sequence
<220> FEATURE:
<223> OTHER INFORMATION: Primer

<400> SEQUENCE: 4
gagaagagct acgagctgcc tgac                                              24

<210> SEQ ID NO 5
<211> LENGTH: 24
<212> TYPE: DNA
<213> ORGANISM: Artificial Sequence
<220> FEATURE:
<223> OTHER INFORMATION: Primer

<400> SEQUENCE: 5
cggagtactt gcgctcagga ggag                                              24

<210> SEQ ID NO 6
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 6

```
Ala Ala Val Ala Leu Leu Pro Ala Val Leu Leu Ala Leu Leu Ala Lys
1               5                   10                  15

Asn Asn Leu Lys Glu Cys Gly Leu Tyr
            20              25

<210> SEQ ID NO 7
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 7

Ala Ala Val Ala Leu Leu Pro Ala Val Leu Leu Ala Leu Leu Ala Lys
1               5                   10                  15

Asn Asn Leu Lys Asp Cys Gly Leu Phe
            20              25
```

COMPOSITIONS AND METHODS WHICH MODULATE G-PROTEIN SIGNALING FOR THE TREATMENT OF INFLAMMATORY DISORDERS SUCH AS ASTHMA AND ALLERGIC CONJUNCTIVITIS

This application is a 35 U.S.C. §365(c) continuation-in-part application of PCT/US09/033581, filed on Feb. 9, 2009, which claims priority under 35 U.S.C. §119(e) to U.S. Provisional Application, 61/026,915, filed Feb. 7, 2008. This application also claims priority under 35 U.S.C. §119(e) to U.S. Provisional Application 61/334,409, filed May 13, 2010. The entirety of the foregoing applications is incorporated by reference herein.

Pursuant to 35 U.S.C. §202(c), it is acknowledged that the United States Government has certain rights in the invention described herein, which was made in part with funds from the National Institutes of Health: Grant Numbers HL-31467, HL-61038 and NIH NHLBI HL097739-01.

FIELD OF THE INVENTION

This invention relates to the fields of signal transduction, respiratory physiology and the treatment or alleviation of the asthmatic condition. More specifically, the invention provides molecules which modulate G protein signaling which, upon delivery to the airway, alleviate the symptoms of asthma. In another aspect, the molecules disclosed can be used to advantage for the treatment of inflammatory ocular disorders, such as allergic conjunctivitis.

BACKGROUND OF THE INVENTION

Several publications and patent documents are cited throughout the specification in order to describe the state of the art to which this invention pertains. Each of these citations is incorporated herein by reference as though set forth in full.

Inhalation of β2-adrenergic receptor (β2AR) agonists in the treatment of asthma is the most effective approach to acutely relieve bronchospasm, reflecting the ability of these agents to dilate the airways by relaxing the surrounding airway smooth muscle (ASM). Chronic use of long-acting β2AR agonists, however, has been associated with heightened bronchoconstrictor responsiveness to airway spasmogens, exacerbation of asthma symptoms, and an increased incidence of asthma-related morbidity and mortality (4,31, 37). This aggravation of the asthmatic condition is thought to result from heightened desensitization of the airways to the bronchodilatory action of β2AR agonists, a phenomenon that is exhibited in isolated asthmatic ASM tissues, together with an increased contractile responsiveness of the tissues to bronchoconstrictor agents (2,3,13). Similarly, naïve ASM tissues and cultured ASM cells exposed to a variety of pro-asthmatic stimuli including atopic asthmatic serum, inflammatory cytokines, and inoculation with rhinovirus, also display attenuated β2AR-mediated relaxation accompanying reduced cAMP generation and increased ASM constrictor responsiveness (20,39). To date, investigations into the etiology of the tolerance of asthmatic airways to β2AR stimulation have largely focused on the potential contributions by mechanisms implicated in mediating homologous (agonist-specific) and/or heterologous (non-agonist-specific) desensitization of the β2AR in ASM (12,39). Accordingly, the role played by phosphorylation of the β2AR by G protein-coupled receptor (GPCR) kinases (GRKs) and cAMP-dependent protein kinase A (PKA) in mediating homologous β2AR desensitization has been demonstrated acutely following exposure of ASM cells to β2AR agonists, and that played by PKA activation in mediating heterologous β2AR desensitization has been demonstrated following more prolonged exposure of ASM to other receptor-coupled or non-receptor-coupled cAMP-elevating agents (12,15,35,39). Collectively, these studies have provided important information regarding the mechanisms involved in uncoupling of the β2AR from its associated Gs protein-mediated accumulation of cAMP, a process resulting in impaired ASM relaxation in the β2AR-desensitized state. These mechanisms notwithstanding, a host of studies conducted on different cell types have demonstrated that the attenuated physiological responses to cAMP-elevating agents detected under conditions associated with homologous or heterologous β2AR desensitization are critically regulated by cAMP phosphodiesterase (PDE) activity (6,9,22,42). Moreover, there is compelling recent evidence that PDE activity plays a crucial role in regulating ASM contractility (33), and in mediating the constrictor hyperresponsiveness of the airways accompanying allergen challenge in asthmatic subjects (43) and in animal models of allergic asthma (8,21,24,41). Little is known, however, regarding the mechanism regulating PDE expression and its role in contributing to the impaired cAMP signaling exhibited in ASM under conditions of prolonged homologous or heterologous β2AR desensitization.

Among the PDE superfamily, isoforms of PDE4 account for most of the cAMP hydrolyzing activity in smooth muscle cells, and PDE4 activity has been importantly implicated in regulating ASM contractility (33). The PDE4 family is encoded by four distinct genes (PDE4A-D) that generate multiple PDE4 enzyme variants through activation of different promoters or alternative splicing. (9,22). The dominant PDE4 type expressed in both vascular smooth muscle and ASM cells is PDE4D and, via alternate promoters, PDE4D can encode six "long" isoforms (PDE4D3-5 and PDE4D7-9) and two PDE4D "short" isoforms (PDE4D1-2) (9,22). Cellular expression of PDE4D is regulated by PKA, and the promoter driving transcription of the functionally dominant long isoform, PDE4D5, in ASM cells contains a cAMP response element (CRE) (5,30). In vascular smooth muscle cells, PDE4D expression was also found to be translationally regulated by PKA, as well as by the MAPK, ERK1/2 (32). Moreover, PKA and ERK1/2 were shown to directly regulate PDE4D catalytic activity (9,22).

SUMMARY OF THE INVENTION

The results presented herein demonstrate that signaling by the Gβγ subunit of Gi protein serves to mediate upregulated PDE4 activity in β2AR-desensitized airway tissues in the associated pro-asthmatic state. Thus, in accordance with the present invention, compositions and methods are provided for delivering Gβγ inhibitors into the airway of patients with asthma, particularly, those patients experiencing symptoms associated with β2-adrenergic receptor desensitization. The compositions of the invention can be directly delivered to the lung, preferably in aerosolized form. They may optionally be combined with one or more conventional agents employed in the treatment of asthma, including without limitation, corticosteroids, sodium cromolyn, methylxanthines, phosphodiesterase inhibitors, beta 2 adrenergic agents, and leukotriene modifiers.

In another embodiment of the invention, the compositions disclosed herein can be used effectively to treat allergic conjunctivitis and other ocular disorders via topical delivery to the eye.

BRIEF DESCRIPTION OF THE DRAWINGS

FIG. 4. PGE2-exposed ASM cells exhibit upregulated PDE4D5 mRNA expression associated with PKA-dependent activation of CREB/ATF1. (A) As detected by RT-PCR, PGE2 (100 nM) elicits temporal increases in PDE4D5 mRNA expression in ASM cells, with peak expression of transcripts detected at 6 hr. (B) Western blot depicting that PGE2 elicits transiently upregulated expression of phosphorylated CREB and ATF1 proteins in ASM cells, with peak phosphorylation detected at 30 min. (C) PGE2-induced phosphorylation of CREB/ATF1 is prevented in ASM cells transfected with siRNA duplexes directed against the PKAα and PKAβ catalytic subunits, whereas transfection with a scrambled (control) siRNA duplex (scRNA) has no effect.

FIG. 7. PGE2-induced phosphorylation of ERK1/2 in ASM cells is mediated by G protein βγ-subunit-mediated activation of the Ras signaling cascade. (A) Western blot depicting that pretreatment with the c-Raf1 inhibitor, GW5074, prevents PGE2-induced phosphorylation of ERK1/2 in ASM cells, whereas inhibition of Rap1 with GGTI-298 has no effect. (B) Western blot showing that, in contrast to ASM cells transfected with adeno-LacZ (i.e., negative control), PGE2-induced ERK1/2 phosphorylation is prevented in ASM cells wherein Gβγ signaling is inhibited by transfection with adeno-βARK-ct.

DETAILED DESCRIPTION OF THE INVENTION

Figure 1:
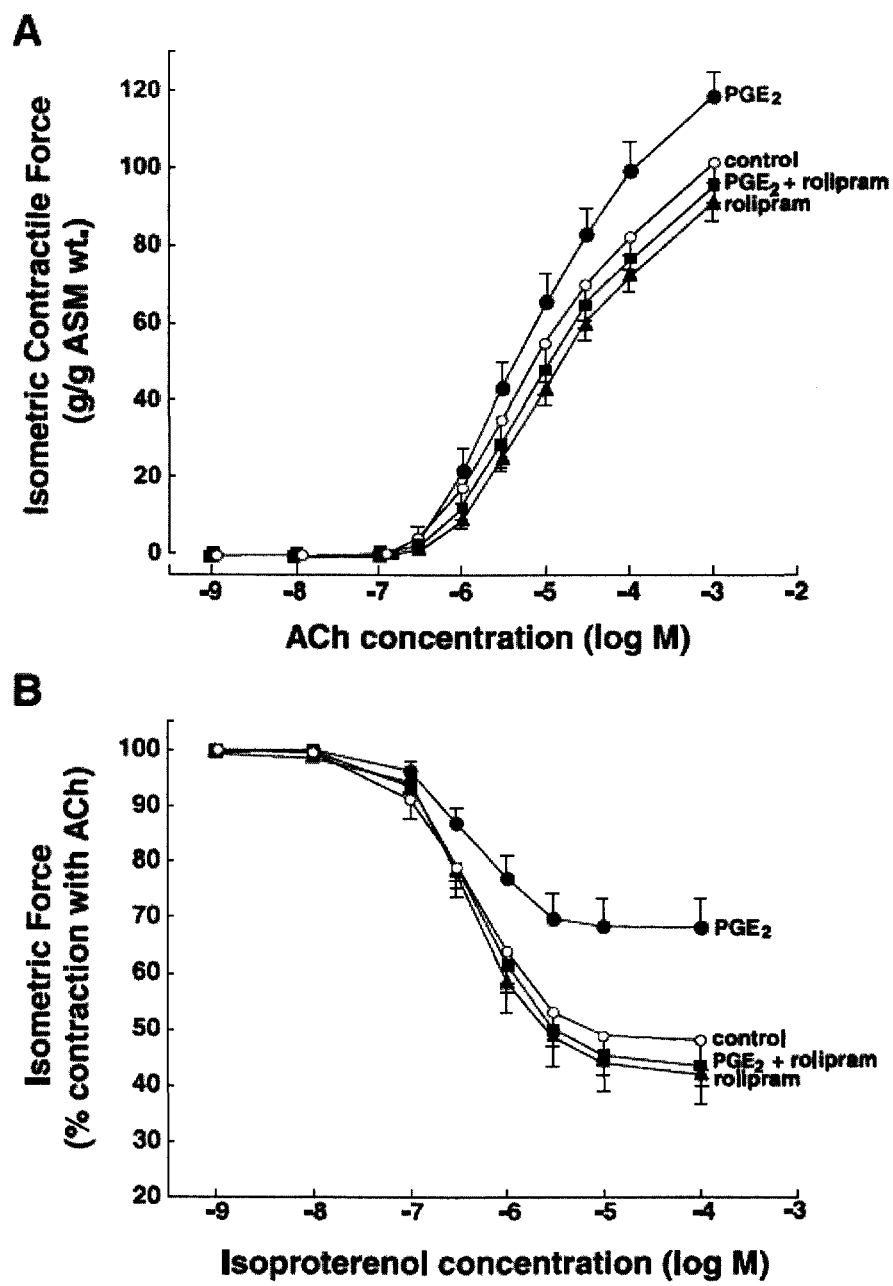
FIG. 1. Inhibition of PDE4 prevents the induction of altered ASM tissue constrictor and relaxation responsiveness accompanying heterologous β2AR desensitization. Relative to vehicle-treated controls, rabbit ASM tissues exposed for 24 hr to prostaglandin (PG)E2 (100 nM) exhibit significantly increased constrictor responses to acetylcholine (ACh) (A) and impaired relaxation responses to isoproterenol (B). Pretreatment with the PDE4 inhibitor, rolipram (10 μM), prevents these PGE2-induced changes in ASM constrictor and relaxation responsiveness, while having no significant effect on ASM responsiveness in vehicle-exposed tissues. Data represent mean±SE values from 5 paired experiments.

β2-adrenergic receptor (β2AR) agonists acutely relieve bonchoconstriction via cAMP-mediated relaxation of airway smooth muscle (ASM). Airway constrictor responsiveness may be significantly heightened, however, following protracted exposure to these agents, presumably reflecting the effects of β2AR-desensitization in ASM accompanying prolonged cAMP signaling. Since cAMP phosphodiesterase (PDE) activity can significantly modulate ASM contractility, the mechanism regulating PDE expression and its potential role in mediating changes in agonist-induced constrictor and relaxation responsiveness was investigated in ASM following heterologous desensitization of its β2AR by prolonged exposure to cAMP-elevating agents.

In accordance with the present invention, the mechanism regulating PDE4 expression and its role in mediating these changes has been elucidated and means of modulating this desensitization are disclosed. The results provide new evidence demonstrating that: 1) desensitization of ASM to β2AR agonists, resulting from its prolonged initial exposure to either receptor- or non-receptor-coupled cAMP elevating agents, evokes increased ASM constrictor responsiveness together with impaired β2AR-mediated ASM relaxation and attenuated cAMP accumulation; 2) these pro-asthmatic-like changes in ASM function are associated with ERK1/2-activation and its induced transcriptional upregulation of PDE4D5 expression via phosphorylation of the CREB and ATF1 transcription factors; and 3) the activation of ERK1/2 is attributed to a PKA-dependent activation of Gi protein-generated signaling via the βγ-subunit of Gi, which leads to downstream activation of the Ras/Raf1/MEK pathway in the β2AR-desensitized state. Collectively, these findings are the first to identify a mechanism that underlies the association between airway tolerance to β2AR agonists and heightened expression of the asthmatic phenotype accompanying prolonged exposure of the airways to cAMP-elevating agents, thereby providing new avenues for the development of efficacious agent(s) for the treatment of asthma.

Thus, the present invention relates to the use of Gβγ inhibitors for the treatment of asthma. In a preferred embodiment localized, aerosolized administration of the Gβγ blocking peptide to the airway and lung provides a higher effective dose than that obtainable via systemic administration. Localized administration of the inhibitor directly to the lung of the patient avoids systemic exposure to the peptide which may result in undesirable secondary side effects. Another advantage of localized aerosolized delivery is that this approach enables administration of lower doses of inhibitor which avoids the inefficient targeting of the Gβγ blocking peptide associated with systemic administration due to clearance by the liver or incomplete absorption in the intestine from oral administration. The compositions and methods are also advantageous in that they provide non-steroidal agents that are effective at alleviating the asthmatic condition.

Aerosolization provides an excellent method for delivering Gβγ blocking peptides. Utilizing this approach, Gβγ peptide inhibitors can be delivered directly in the local environment of the airway as an aerosol, thereby directly targeting airway smooth muscle cells. Inclusion of a membrane permeant peptide sequence (MPS) from the signal sequence of Karposi fibroblast growth factor to the Gβγ blocking peptide facilitates entry of the inhibitor into the cells in the airway.

In one embodiment of the present invention, G protein signaling is modulated using a Gβγ blocking peptide. An exemplary blocking peptide attached to a membrane permeable carrier peptide has the following letter code sequence:

```
                                            (SEQ ID NO: 1)
AAVALLPAVLLALLAVTDQLGEDFFAVDLEAFLQEFGLLPEKE;.
```

Other cell-penetrating peptides and proteins for use in the invention are known in the art, as described in Kinyanjui et al. (Can. J. Physiol. Pharmacol. (2008) 86:1-7).

In other embodiments of the invention, inhibitors of Gβγ signaling can include cyclohexanecarboxylic acid [2-(4,5,6-trihydroxy-3-oxo-3H-xanthen-9-yl)-(9Cl)], gallein, M119, βARKct, phosducin fragment containing amino acids 217-246, and phosducin fragment containing amino acids 213-233, and those described in Smrcka (Cell. Mol. Life Sci. (2008) 65:2191-2214. In certain embodiments, the inhibitor of Gβγ signaling can be linked to a membrane permeable carrier.

Exemplary methods entail delivering Gβγ blocking peptides into patients with asthma, including those patients experiencing symptoms associated with β2-adrenergic receptor desensitization. The compositions of the invention can be directly delivered to the lung, as opposed to previous studies which have not investigated delivery to the pulmonary system.

Thus, a new approach for treating asthma is described herein. The peptides of the invention may be used alone or combined with other agents used to treat asthma or genes encoding proteins to augment the anti-asthmatic/anti-inflammatory efficacy of the peptides.

The present inventor has also discovered that the compositions described herein are effective for ameliorating the symptoms of allergic conjunctivitis and other ocular disorders associated with aberrant beta adrenergic signaling.

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.") are used.

I. Definitions

The following definitions are provided to facilitate an understanding of the present invention:

As used herein, the term "Gβγ inhibitor" refers to any molecule or compound which is able to disrupt G protein βγ interactions and thereby impede downstream signaling. For example, a "G βγ blocking peptide" refers to a peptide which targets Gβγ subunits, mimics the protein binding domains thereof and blocks their interaction. Such "blocking peptides" also include a membrane permeant peptide sequence. Additional Gβγ inhibitors include, without limitation, the carboxy terminus of the BARK protein (BARK-ct as shown in FIG. 7 herein), βγ peptide inhibitors comprising fragments of phosducin e.g. amino acids 217-246 and amino acids 213-233 such as those described in EP 0 896 965 A1 and the alpha subunit of transducin protein. Ideally each of the aforementioned inhibitors will be operably linked to a membrane permeable peptide sequence to facilitate entry into cells surrounding the airway, including the airway smooth muscle cells.

A "membrane permeant peptide sequence" refers to a peptide sequence which is able to facilitate penetration and entry of the Gβγ inhibitor across the cell membrane. Exemplary peptides include without limitation, the signal sequence from Karposi fibroblast growth factor exemplified herein, the HIV tat peptide (Vives et al., J Biol. Chem., 272:16010-16017, 1997), Nontoxic membrane translocation peptide from protamine (Park et al. FASEB J. 19(11):1555-7, 2005), CHARIOT® delivery reagent (Active Motif; U.S. Pat. No. 6,841,535) and the antimicrobial peptide Buforin 2.

By the term "asthmatic state" as used herein, is meant the proasthmatic phenotype which is observed in airway smooth muscle cells. This phenotype is characterized by increased contraction and decreased relaxation of the airway tissue when it has been exposed for extended time periods to cAMP-elevating agents such as beta2-adrenergic agonists, pro-asthmatic stimuli such as specific cytokines, high IgE-containing atopic asthmatic serum or exogenous IgE, compared with airway tissue which has not been exposed to these agents or stimuli. By the term "treating asthma" is meant curing asthma, causing the symptoms of asthma to diminish, ablating or otherwise alleviating the disease.

The term "aerosol formulation" refers to a pharmaceutical composition suitable for administration through the respiratory system or nasal passages. Examples of aerosol formulations are described below. Similarly, the term "aerosol administration" is intended to refer to a mode of administering an aerosol formulation to the respiratory system or nasal passages.

The invention provides a composition of matter comprising an aerosol formulation of the inhibitor where the Gβγ blocking peptides is present at a concentration ranging from 0.001 mg to 1000 mg. Peptides of the invention can be functional fragments of proteins.

"Peptide" and "polypeptide" are used interchangeably herein and refer to a compound made up of a chain of amino acid residues linked by peptide bonds. The sequence for peptides is given in the order from the amino terminus to the carboxyl terminus. A peptide or peptide fragment is "derived from" a parent peptide or polypeptide if it has the amino acid sequence that is identical or homologous to the amino acid sequence of the parent peptide or polypeptide.

The term "substantially pure" refers to a preparation comprising at least 50-60% by weight of a given material (e.g., peptide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

"Inflammation-controlling effective amount" refers to the amount of the pharmaceutically active substance sufficient to elicit at least a desired threshold response to the substance in a subject to which the substance is administered, whether therapeutic or prophylactic.

The term "functional" as used herein implies that the nucleic or amino acid sequence is functional for the recited assay or purpose.

The phrase "consisting essentially of" when referring to a particular amino acid means a sequence having the properties of a given SEQ ID NO. For example, when used in reference to an amino acid sequence, the phrase includes the sequence per se and molecular modifications that would not affect the essential and novel characteristics of the sequence.

As disclosed herein, Gβγ blocking peptides are effective at reducing a sign or symptom of asthma and allergic conjunctivitis and thus are useful for the treatment thereof. The compositions of the invention are effective at inhibiting pro-asthmatic changes in airway smooth muscle tissue and may also be effective for treatment of allergic rhinitis, atopic dermatitis and possibly non-allergic rhinitis and dermatitis induced by chemical irritants.

II. Pharmaceutical Compositions

Methods of the invention directed to treating asthma involve the administration of a Gβγ inhibitor in a pharmaceutical composition. A G βγ inhibitor is administered to an individual as a pharmaceutical composition comprising a Gβγ inhibitor and a pharmaceutically acceptable carrier. Pharmaceutically acceptable carriers are well known in the art and include aqueous solutions such as physiologically buffered saline, other solvents or vehicles such as glycols, glycerol, oils such as olive oil or injectable organic esters.

A pharmaceutically acceptable carrier can contain physiologically acceptable compounds that act, for example, to stabilize the Gβγ blocking peptide or increase the absorption of the agent. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the Gβγ blocking peptide and on the particular physico-chemical characteristics of the peptide.

One skilled in the art appreciates that a pharmaceutical composition comprising a Gβγ blocking peptide can be administered to a subject by various routes including, for example, orally or parenterally, such as intravenously (i.v.), intramuscularly, subcutaneously, intraorbitally, intranasally, intracapsularly, intraperitoneally (i.p.), intracisternally, intratracheally (i.t), or intra-articularly or by passive or facilitated absorption, and most preferably, using a nasal spray or inhalant.

Administration of a Gβγ inhibitor by inhalation is a particularly preferred means of treating an individual having asthma. One skilled in the art would recognize that a Gβγ blocking peptide can be suspended or dissolved in an appropriate pharmaceutically acceptable carrier and administered, for example, directly into the lungs using a nasal spray or inhalant.

A pharmaceutical composition comprising a Gβγ peptide inhibitor can be administered as an aerosol formulation which contains the inhibitor in dissolved, suspended or emulsified form in a propellant or a mixture of solvent and propellant. The aerosolized formulation is then administered through the respiratory system or nasal passages.

An aerosol formulation used for nasal administration is generally an aqueous solution designed to be administered to the nasal passages in drops or sprays. Nasal solutions are generally prepared to be similar to nasal secretions and are generally isotonic and slightly buffered to maintain a pH of about 5.5 to about 6.5, although pH values outside of this range can additionally be used. Antimicrobial agents or preservatives can also be included in the formulation.

An aerosol formulation used for inhalations and inhalants is designed so that the Gβγ blocking peptide is carried into the respiratory tree of the patient administered by the nasal or oral respiratory route. Inhalation solutions can be administered, for example, by a nebulizer. Inhalations or insufflations, comprising finely powdered or liquid drugs, are delivered to the respiratory system as a pharmaceutical aerosol of a solution or suspension of the drug in a propellant.

An aerosol formulation generally contains a propellant to aid in disbursement of the Gβγ blocking peptide. Propellants can be liquefied gases, including halocarbons, for example, fluorocarbons such as fluorinated chlorinated hydrocarbons, hydrochlorofluorocarbons, and hydrochlorocarbons as well as hydrocarbons and hydrocarbon ethers (Remington's Pharmaceutical Sciences 18th ed., Gennaro, A. R., ed., Mack Publishing Company, Easton, Pa. (1990)).

Halocarbon propellants useful in the invention include fluorocarbon propellants in which all hydrogens are replaced with fluorine, hydrogen-containing fluorocarbon propellants, and hydrogen-containing chlorofluorocarbon propellants. Halocarbon propellants are described in Johnson, U.S. Pat. No. 5,376,359, and Purewal et al., U.S. Pat. No. 5,776,434.

Hydrocarbon propellants useful in the invention include, for example, propane, isobutane, n-butane, pentane, isopentane and neopentane. A blend of hydrocarbons can also be used as a propellant. Ether propellants include, for example, dimethyl ether as well as numerous other ethers.

The Gβγ blocking peptide can also be dispensed with a compressed gas. The compressed gas is generally an inert gas such as carbon dioxide, nitrous oxide or nitrogen.

An aerosol formulation of the invention can also contain more than one propellant. For example, the aerosol formulation can contain more than one propellant from the same class such as two or more fluorocarbons. An aerosol formulation can also contain more than one propellant from different classes. An aerosol formulation can contain any combination of two or more propellants from different classes, for example, a fluorohydrocarbon and a hydrocarbon.

Effective aerosol formulations can also include other components, for example, ethanol, isopropanol, propylene glycol, as well as surfactants or other components such as oils and detergents (Remington's Pharmaceutical Sciences, 1990; Purewal et al., U.S. Pat. No. 5,776,434). These aerosol components can serve to stabilize the formulation and lubricate valve components.

The aerosol formulation can be packaged under pressure and can be formulated as an aerosol using solutions, suspensions, emulsions, powders and semisolid preparations. A solution aerosol consists of a solution of an active ingredient such as a Gβγ blocking peptide in pure propellant or as a mixture of propellant and solvent. The solvent is used to dissolve the active ingredient and/or retard the evaporation of the propellant. Solvents useful in the invention include, for example, water, ethanol and glycols. A solution aerosol contains the active ingredient peptide and a propellant and can include any combination of solvents and preservatives or antioxidants.

An aerosol formulation can also be a dispersion or suspension. A suspension aerosol formulation will generally contain a suspension of an effective amount of the Gβγ blocking peptide and a dispersing agent. Dispersing agents useful in the invention include, for example, sorbitan trioleate, oleyl alcohol, oleic acid, lecithin and corn oil. A suspension aerosol formulation can also include lubricants and other aerosol components.

An aerosol formulation can similarly be formulated as an emulsion. An emulsion can include, for example, an alcohol such as ethanol, a surfactant, water and propellant, as well as the active ingredient Gβγ blocking peptide. The surfactant can be nonionic, anionic or cationic. One example of an emulsion can include, for example, ethanol, surfactant, water and propellant. Another example of an emulsion can include, for example, vegetable oil, glyceryl monostearate and propane.

An aerosol formulation containing a Gβγ blocking peptide will generally have a minimum of 90% of the particles in inhalation products between about 0.5 and about 10 μm to maximize delivery and deposition of the Gβγ blocking peptide to respiratory fluids. In particular, the particle size can be from about 3 to about 6 μm.

A pharmaceutical composition comprising a Gβγ blocking peptide inhibitor also can be incorporated, if desired, into liposomes, microspheres, microbubbles, or other polymer matrices (Gregoriadis, Liposome Technology, Vols. I to III, 2nd ed., CRC Press, Boca Raton Fla. (1993)). Liposomes, for example, which consist of phospholipids or other lipids, are nontoxic, physiologically acceptable and metabolizable carriers that are relatively simple to make and administer.

In order to treat an individual having asthma, to alleviate a sign or symptom of the disease, a Gβγ blocking peptide should be administered in an effective dose. The total treatment dose can be administered to a subject as a single dose or can be administered using a fractionated treatment protocol, in which multiple doses are administered over a more prolonged period of time, for example, over the period of a day to allow administration of a daily dosage or over a longer period of time to administer a dose over a desired period of time. One skilled in the art would know that the amount of a Gβγ blocking peptide required to obtain an effective dose in a subject depends on many factors, including the age, weight and general health of the subject, as well as the route of administration and the number of treatments to be administered. In view of these factors, the skilled artisan would adjust the particular dose so as to obtain an effective dose for treating an individual having asthma.

The effective dose of a Gβγ blocking peptide will depend on the mode of administration, and the weight of the individual being treated. The dosages described herein are generally those for an average adult but can be adjusted for the treatment of children. The dose will generally range from about 0.001 mg to about 1000 mg.

The concentration of a Gβγ blocking peptide in a particular formulation will depend on the mode and frequency of administration. A given daily dosage can be administered in a single dose or in multiple doses so long as the Gβγ blocking peptide concentration in the formulation results in the desired daily dosage. One skilled in the art can adjust the amount of Gβγ blocking peptide in the formulation to allow administration of a single dose or in multiple doses that provide the desired concentration of Gβγ inhibitor over a given period of time.

In an individual suffering from asthma, in particular a more severe form of the disease, administration of a Gβγ blocking peptide can be particularly useful when administered in combination, for example, with a conventional agent for treating such a disease. The skilled artisan would administer a Gβγ blocking peptide, alone or in combination with a second agent, based on the clinical signs and symptoms exhibited by the individual and would monitor the effectiveness of such treatment using routine methods such as pulmonary function determination, radiologic, immunologic or, where indicated, histopathologic methods.

A Gβγ blocking peptide can be administered in combination with steroidal anti-inflammatory agents including corticosteroids, for example, dexamethasone, beclomethasone, fluticasone, triamcinolone and budesonide. A Gβγ inhibitor can also be administered in combination with non-steroidal anti-inflammatory agents such as, indomethacin, ibuprofen, naproxen, diclofenac, sulindac, oxaprozin, diflunisal, bromfenac, piroxicam, etodolac and fenoprofen. Inhibitor administration can also be combined with short- and long-acting β2-adrenergic agents such as albuterol and salmeterol, respectively, as the inhibitor alleviates the desensitization to the β2-adrenoreceptor agent. When a Gβγ blocking peptide is used with another anti-inflammatory agent, the Gβγ inhibitor can generally be administered at a lower dosage. For example, a Gβγ inhibitor can be administered at a dose of less than 10 mg per day in combination with another anti-inflammatory agent.

When a Gβγ blocking peptide is administered in combination with one or more other anti-inflammatory agent, the Gβγ blocking peptide and other anti-inflammatory agent can be co-administered in the same formulation. Alternatively, the Gβγ blocking peptide and other anti-inflammatory agent can be administered simultaneously in separate formulations. In addition, the Gβγ blocking peptide can be administered in separate formulations, where the separate formulations are not administered simultaneously but are administered during the same period of treatment, for example, during a daily or weekly period of treatment. Alternatively, each agent may be given sequentially during a daily or weekly period of treatment.

Administration of the pharmaceutical preparation is preferably in a "prophylactically effective amount" or a "therapeutically effective amount" (as the case may be, although prophylaxis may be considered therapy), this being sufficient to show benefit to the individual. This amount prevents, alleviates, abates, or otherwise reduces the severity of symptoms in a patient.

The pharmaceutical preparation is formulated in dosage unit form for ease of administration and uniformity of dosage. Dosage unit form, as used herein, refers to a physically discrete unit of the pharmaceutical preparation appropriate for the patient undergoing treatment. Each dosage should contain a quantity of active ingredient calculated to produce the desired effect in association with the selected pharmaceutical carrier. Procedures for determining the appropriate dosage unit are well known to those skilled in the art.

Dosage units may be proportionately increased or decreased based on the weight of the patient. Appropriate concentrations for alleviation of a particular pathological condition may be determined by dosage concentration curve calculations, as known in the art. As mentioned previously, a preferred embodiment of the invention comprises aerosolized delivery of the Gβγ blocking peptide to the lungs of a patient in need thereof. The Gβγ blocking peptide described herein can also be injected intra-peritoneally (i.p.), intravenously (i.v.), or intratracheally (i.t.). Formulation, dosages and treatment schedules have also been described hereinabove.

Ocular Administration of the Composition of the Invention

Typically the compositions of the subject invention are prepared as solutions, suspensions, ointments, gels, or ocular delivery devices such as drug-impregnated solid carriers that are inserted into the eye. If such a carrier is used, the above-mentioned vehicles are unnecessary. A variety of polymers can be used to formulate ophthalmic drug carriers. Saettone, M. F., et al., J. Pharm. Pharmacol. (1984) 36:229, and Park, K. et al., in Recent Advances in Drug Delivery Systems, Anderson et al, eds., Plenum Press (1984) 163-183, describe such polymers, the disclosures of which are incorporated herein by reference in their entirety. Drug release is generally effected via dissolution or bioerosion of the polymer, osmosis, or combinations thereof. The device should be formulated to release the drug at a rate that does not significantly disrupt the tonicity of tear fluid.

More specifically, several matrix-type delivery systems can be used with the subject invention. These systems are described in detail in Ueno et al., "Ocular Pharmacology of Drug Release Devices", in Controlled Drug Delivery, Bruck, ed., vol. II, Chap 4, CRC Press Inc. (1983), the disclosure of which is incorporated herein by reference in its entirety. Such systems include hydrophilic soft contact lenses impregnated or soaked with the desired drug, as well as biodegradable or soluble devices that need not be removed after placement in the eye. These soluble ocular inserts can be composed of any degradable substance that can be tolerated by the eye and that is compatible with the drug to be administered. Such substances include but are not limited to poly(vinyl alcohol), polymers and copolymers of polyacrylamide, ethylacrylate, and vinylpyrrolidone, as well as cross-linked polypeptides or polysaccharides, such as chitin.

Capsule-type delivery systems will also find use with the instant invention. These systems, described in Ueno et al., supra, utilize polymer membranes to control the release of the drug in question. These devices are particularly useful for the delivery of hydrophilic drugs. Hydrophobic drugs can be administered via a silicone rubber device such as described in Ueno et al., supra.

Ophthalmic ointments will include a base, generally composed of white petrolatum and mineral oil, often with anhydrous lanolin. Polyethylene-mineral oil gel is also satisfactory, as are other substances that are non-irritating to the eye, permit diffusion of the drug into the ocular fluid, and retain activity of the medicament for a reasonable period of time under storage conditions. If suspensions are used, the particle sizes therein should be less than 10 μm to minimize eye irritation. Furthermore, if solutions or suspensions are used, the amount delivered to the patient should not exceed 50 μl, preferably 25 μl or less, to avoid excessive spillage from the eye.

The examples set forth below are provided to illustrate certain embodiments of the invention. They are not intended to limit the invention in any way.

The following materials and methods are provided to facilitate the practice of the Examples below.

Materials: All chemicals were purchased from Sigma-Aldrich unless otherwise indicated. The human ASM cells were obtained from BioWhittaker, Inc., Animals: Adult New Zealand White rabbits were used in this study, which was approved by the Biosafety and Animal Research Committee of the Joseph Stokes Research Institute at Children's Hospital of Philadelphia. The animals had no signs of respiratory disease for several weeks before the study, and their care and use were in accordance with the "Guide for the Care and Use of Laboratory Animals" prepared by the Institute of Laboratory Animal Resources, National Research Council.

Culture and treatment of ASM cells: The human ASM cells were grown in SmBm media supplemented with 10% FBS (BioWhittaker) and maintained throughout in a humidified incubator containing 5% $CO_2$ in air at 37° C. The experimental protocols involved growing the cells to ~95% confluence in the above medium. Thereafter, in separate experiments, the cells were starved in unsupplemented Ham's F12 media for 24 hr, treated with different concentrations and for varying durations with PGE2 or forskolin (heterologous desensitization) or salmeterol or isoproterenol (homologous desensitization), and then examined for induced changes in PDE activity, ERK1/2 and CREB/ATF1 phosphorylation, and PDE4D5 mRNA expression in the absence and presence of specific inhibitors, as described.

Assay of cAMP accumulation: In initial studies, intracellular cAMP levels were determined in near confluent ASM cell cultures at varying times following treatment of ASM cells with varying concentrations of isoproterenol (0.1 to 100 μM). In subsequent experiments, cells were pretreated for 24 hr with either vehicle alone or PGE2 (100 μM), both in the absence and presence of rolipram (10 μM). Following pretreatment, cells were exposed for 5 min to isoproterenol (10 μM) at 37° C., and intracellular cAMP accumulation was quantified by radioimmunoassay, as previously described (19).

In additional experiments, cells were pretreated for 24 h with either vehicle alone or salmeterol (10 μM), both in the absence and presence of rolipram (10 μM). Thereafter, in the continued presence of these treatments, cells were exposed for 5 min to isoproterenol (10 μM) at 37° C., and intracellular cAMP concentrations were determined per manufacturer's protocols using a direct cAMP Enzyme Immunoassay Kit (R&D Systems, Minneapolis, Minn.). In both cases, the cAMP measurements were expressed in units of picomoles/milligram protein.

Assay of cAMP PDE activity: Levels of cAMP PDE activity were assayed in ASM cell lysates using a colorimetric, non-radioactive enzymatic assay kit from Biomol, as per the manufacture's protocol. PDE activity was determined following exposure of ASM cells for 24 hr to either vehicle alone (control), PGE2 (100 μM), or forskolin (100 μM) in the absence and presence of pretreatment with rolipram (10 μM), cycloheximide (100 μM), actinomycin D (4 μM), or H89 (10 μM).

In additional experiments, PDE activity was determined following exposure of ASM cells for 24 hr to either vehicle alone (control), salmeterol (10 μM) or isoproterenol (10 μM), in the absence and presence of pre-treatment with rolipram (10 μM), cycloheximide (100 μM), actinomycin D (4 μM), H89 (10 μM), U0126 (5 μM), Pertussis toxin (100 ng/ml), anti-α3 peptide MPS (1 μM) or anti-βγ peptide MPS-phosducin-like protein (1 μM) from AnaSpec, Inc. (San Jose, USA). In each case, the measured levels of PDE activity were standardized to the protein content in the cell extracts.

Detection of PDE4D5 mRNA transcripts: Total RNA was extracted from the cultured ASM cells using the TRIzol method (Invitrogen), and cDNAs were isolated by RT-PCR using the SuperScript First Strand Synthesis System kit from Invitrogen, with the following oligonucleotide primer sets (Integrated DNA Technologies): for PDE4D5, 5'-TGC-CAGCTGTACAAAGTTGACC-3' (forward; SEQ ID NO: 2) and 5'-TTCTCGGAGAGATCACTGGAGA-3' (reverse; SEQ ID NO: 3); and for β-actin, 5'-GAGAAGAGCTAC-GAGCTGCCTGAC-3' (forward; SEQ ID NO: 4) and 5'-CG-GAGTACTTGCGCTCAGGAGGAG-3' (reverse; SEQ ID NO: 5). The reaction volume was 20 μl and cycling conditions used were 35 cycles of 30 sec denaturation at 95° C., followed by 30 sec annealing at 60° C. and elongation at 72° C. for 30 sec. Ex-Tag (Takara Biotechnology) was used as DNA polymerase.

Immunoblot analysis of CREB/ATF1 and ERK1/2 activation: Levels of phosphorylated CREB, ATF1, and ERK1/2 protein were detected by Western blot analysis of lysates isolated from ASM cells before and at various times after treatment with PGE2, isoproterenol or salmeterol in the absence and presence of specific inhibitors, as described. Following protein extraction and the addition of gel-loading buffer, the extracts were loaded on a 10% SDS-PAGE gel for immunoblotting after transfer to a PVDF membrane. The membranes were then incubated overnight with monoclonal mouse anti-human primary antibodies directed against phospho-CREB and -ATF1, phospho-ERK1/2, or α-actin, and levels were detected by ECL after a 1-hr incubation with a 1:2,000 dilution of HRP-conjugated rabbit anti-mouse secondary antibody, followed by exposure to autoradiography film. The protein band intensities were quantified by densitometry.

siRNA-mediated knockdown of PKA: ASM cells were seeded into 6-well plates and, at ~40% confluency, the medium was replaced with the reduced serum-containing medium, Opti-MEM (Invitrogen). The cells were then transfected twice during a 24-hr interval with two pools of three siRNA duplexes, each pool targeted against the human PKAα or PKAγ catalytic subunits (Santa Cruz Biotechnology; sc-36240 and sc-36236, respectively), or with a non-targeted control (scrambled) siRNA duplex, using Oligofectamine (Invitrogen) as the transfection agent. The pools of siRNAs were applied to each well at a final concentration of 100 nM for each siRNA preparation. Based on preliminary studies, this double-transfection approach was found to greatly enhance transfection efficiency and, as detected by Western blot analysis, markedly inhibited PKAα expression by the targeted siRNA duplexes, with maximal inhibition detected at 72 hr following siRNA transfection.

Transfection of ASM cells with adeno-βARK-ct: Adenovirus (adeno)-βARK-ct, an adenovirus vector encoding the βARK1 carboxyl-terminal domain which blocks Gβγ signaling (25,26), and adeno-β-gal, an adenovirus vector expressing lacZ as a negative control, were constructed using the AdenoX adenovirus construction kit (BD-Clontech). Recombinant plaques were isolated and propagated in HEK293 cells (Invitrogen), with viral purification using the cesium chloride gradient method, and viral titer detected by plaque assay. The ASM cells were transfected with either of the adenoviral vectors at a multiplicity of infection (MOI) of 100, and experiments were conducted at 24 hr following adenoviral tranfections.

Pharmacodynamic studies of constrictor and relaxation responsiveness in rabbit ASM tissues: Following initial sedation and subsequent general anesthesia with intramuscular injections of xylazine (10 mg/kg) and ketamine (50 mg/kg), respectively, rabbits were sacrificed with an intravenously administered overdose of sodium pentobarbital (100 mg/kg). As described previously (16), the tracheae were excised via open thoracotomy, the loose connective tissue and epithelium were scraped and removed, and the tracheae were divided into 8 ring segments, each of 6-8 mm in length. The airway segments were then placed in modified Krebs-Ringer solution containing indomethacin (10 μM), and each alternate ring was incubated for 24 hr at room temperature in the presence of either vehicle alone (control) or varying concentrations of $PGE_2$ or salmeterol, each in the absence and presence of either rolipram (10 μM), the PKA inhibitor, H89 (10 μM), the MEK-ERK1/2 inhibitors, U0126 (5 μM), or pertussis toxin (100 ng/ml). In the homologous desensitization experiments using salmeterol, the cells were also incubated in the presence of an anti-Giα3 peptide coupled to a membrane-permeable sequence (MPS) (30 μM) or an anti-βγ peptide coupled to MPS (30 μM) from AnaSpec, Inc. (San Jose, USA). After these incubations, the tissues were placed in organ baths containing modified Krebs-Ringer solution aerated with 5% $CO_2$ in oxygen (pH of 7.35-7.40), and attached to force transducers to continuously monitor isometric tension. Cholinergic contractility was then assessed in the tissues following cumulative administration of acetylcholine (ACh) in final bath concentrations ranging from $10^{-9}$ to $10^{-3}$ M. The tissues were then repeatedly rinsed with fresh buffer, and relaxation dose-response curves to isoproterenol ($10^{-9}$-$10^{-4}$ M) were generated after the tissues were half-maximally contracted with their respective ED50 doses of ACh. The constrictor and relaxation dose-response curves were analyzed with respect to each tissue's maximal isometric contractile force (Tmax) to ACh and maximal relaxation response (Rmax) to isoproterenol from the initial level of active cholinergic contraction. Statistical analyses: Results are expressed as mean±SE values. Comparisons between groups were made using the Student's t-test (two-tailed) or ANOVA with Tukey's post-test analysis, where appropriate. A probability of <0.05 was considered statistically significant. Statistical analyses were conducted using the Prism computer program by GraphPad Software Inc.

EXAMPLE I

Prolonged Heterologous β-Adrenergic Receptor Desensitization Elicits Pro-Asthmatic Airway Smooth Muscle Function Via Gi-βγ-Mediated Upregulation of Phosphodiesterase-4

Role of PDE4 in Regulating Constrictor and Relaxation Responsiveness in β2AR-Desensitized ASM.

To assess the role of PDE4 in mediating the effects of heterologous β2AR desensitization on ASM function, constrictor responses to ACh and relaxation responses to isoproterenol, which acts via β2AR activation in ASM, were compared in isolated rabbit ASM tissues exposed for 24 hr to either vehicle alone (control) or to a pre-determined maximally effective concentration of PGE2 (100 nM), both in the absence and presence of pretreatment of the tissues with the PDE4-selective inhibitor, rolipram (10 μM). Relative to their respective vehicle-treated controls, ASM tissues exposed to PGE2 exhibited significantly increased constrictor responsiveness to exogenously administered ACh (FIG. 1A), yielding a mean±SE maximal constrictor response (Tmax) value of 119.3±5.9 g/g ASM wt. vs. the value of 101.2±6.1 g/g ASM wt. obtained in the control tissues (p<0.05). This enhanced constrictor responsiveness to ACh was completely abrogated in PGE2-exposed tissues that were pretreated with rolipram. Under the same treatment conditions, during subsequent sustained half-maximal contraction of the tissues with ACh, administration of isoproterenol produced cumulative dose-dependent relaxation of the pre-constricted ASM segments. Relative to control tissues, the relaxation responses to isoproterenol were significantly attenuated in the PGE2-exposed ASM segments (FIG. 1B), consistent with their development of heterologous β2AR desensitization. Accordingly, the mean±SE maximal relaxation (Rmax) response in the PGE2-exposed tissues amounted to 31.4±5.4% vs. the average Rmax value of 51.5±5.5% obtained in the control ASM segments (p<0.01). This impaired relaxant responsiveness to isoproterenol was also completely ablated in PGE2-exposed tissues that were pretreated with rolipram. As further depicted in FIG. 1, relative to the control preparations, ASM tissues that were treated with rolipram alone (filled triangles) showed only modestly decreased constrictor responses to ACh and increased relaxation responses to isoproterenol, with neither of these changes being statistically significant.

As with PGE2, heterologous β2AR desensitization conferred by prolonged exposure to forskolin (100 μM×24 hr), an agent that stimulates cAMP accumulation via direct (non-receptor-mediated) activation of adenylyl cyclase, also evoked significant increases in ASM constrictor responsiveness to ACh and impaired relaxation responsiveness to isoproterenol. Moreover, these effects were also completely abrogated by pretreating the forskolin-exposed ASM tissues with rolipram (data not shown).

Role of PDE4 in Regulating Altered cAMP Responses in β2AR-Desensitized ASM Cells.

Figure 2:
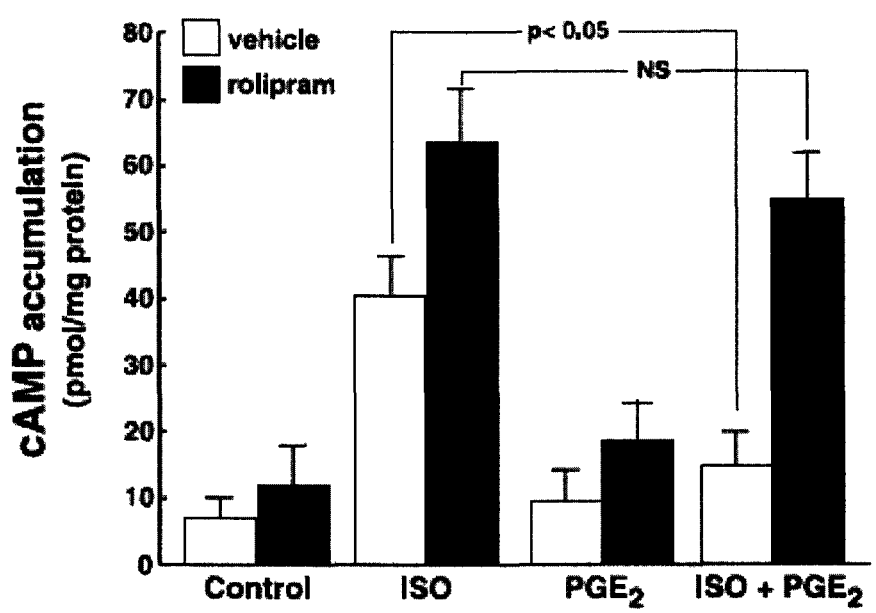
FIG. 2. Inhibition of PDE4 prevents the induction of impaired β2AR-mediated cAMP accumulation accompanying heterologous β2AR desensitization in cultured human ASM cells. In vehicle-exposed ASM cells (open bars), isoproterenol (ISO; 1.0 μM) acutely elicits cAMP accumulation, and the magnitude of this response is significantly attenuated in PGE2-exposed cells ($p<0.05$). By comparison, in ASM cells pretreated with rolipram (10 μM; hatched bars), the cAMP responses to isoproterenol are increased, and unaltered by pre-exposing the cells to PGE2. Data represent mean±SE values from 3 experiments.

Next, the changes in ASM constrictor and relaxation responsiveness obtained in the β2AR-desensitized state were examined to determine if they are reflective of rolipram-sensitive changes in β2AR agonist-induced cAMP accumulation. In these studies, acute changes in intracellular cAMP accumulation detected at 5 min following administration of a near half-maximal effective concentration of isoproterenol (1.0 μM) were compared in confluent cultures of ASM cells that were pretreated for 24 hr either with vehicle alone or PGE2 (100 nM), both in the absence and presence of pretreatment with rolipram (10 μM). As shown in FIG. 2, in the absence of rolipram (open bars), the PGE2-exposed ASM cells exhibited heterologous β2AR desensitization, as evidenced by significantly reduced cAMP responses to isoproterenol relative to those detected in cells that were not exposed to the prostanoid. Contrasting these observations, ASM cells pretreated with rolipram (filled bars) exhibited increased isoproterenol-induced cAMP accumulation, and this response was preserved in the PGE2-exposed cells. Thus, in concert with the results obtained in rabbit ASM tissues, these observations implicate PDE4 activity in mediating the impaired isoproterenol-induced accumulation of cAMP accompanying heterologous β2AR desensitization in human ASM cells.

Regulation of cAMP PDE Activity in β2AR-Desensitized ASM Cells.

Figure 3:
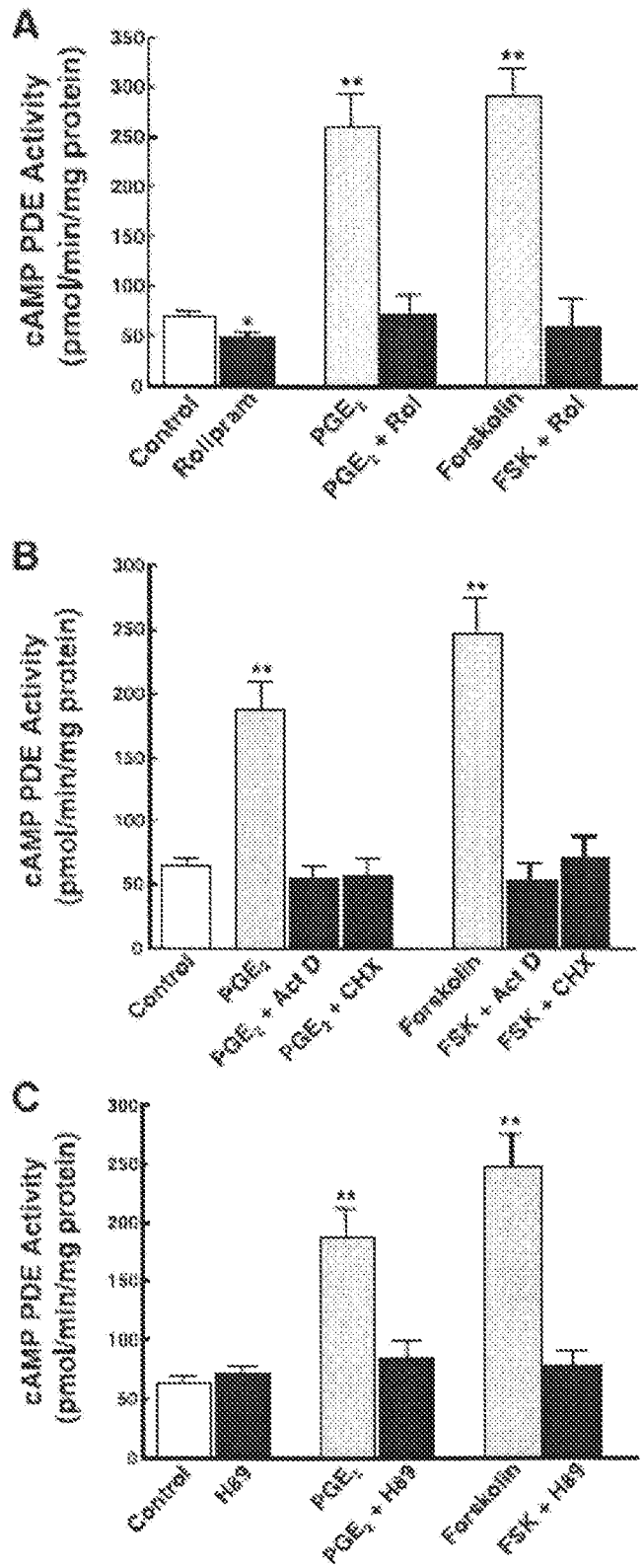
FIG. 3. Regulation of cAMP PDE4 activity in cultured human ASM cells exposed to PGE2 and forskolin. Relative to vehicle-treated (control) ASM cells, levels of PDE4 activity are significantly increased in cells exposed for 24 hr to 100 nM of PGE2 or forskolin. The stimulated PDE activity is ablated in PGE2- and forskolin-exposed ASM cells by pretreatment either with the PDE4 inhibitor, rolipram (A), the transcription or protein synthesis inhibitors, actinomycin D (Act D) and cycloheximide (CHX), respectively (B), or the PKA inhibitor, H89 (C). Data represent mean±SE values based on 3-4 measurements obtained under each treatment condition. *$p<0.05$; **$p<0.01$.

To elucidate the mechanism underlying the above rolipram-sensitive changes in ASM function, total cAMP PDE activity and the effects of selective inhibitors on this activity were examined in cultured human ASM cells following their prolonged exposure to PGE2 or forskolin. Relative to the mean (±SE) basal level of PDE activity detected in vehicle-treated (control) cells (i.e., 69.5±4.8 pmol/min/mg protein), ASM cells incubated for 24 hr with 100 μM of PGE2 or forskolin exhibited significantly increased levels of PDE activity that averaged 3.74- and 4.01-fold above control, respectively (FIG. 3A). These stimulatory effects on PDE activity were completely abrogated in PGE2- and forskolin-exposed cells that were pretreated with rolipram (10 μM), implying that the augmented PDE activity exhibited by the β2AR-desensitized cells was attributed to PDE4. In separate experiments, inclusion of the transcriptional inhibitor, actinomycin D (4 μM), or the protein synthesis inhibitor, cycloheximide (100 μM), in the ASM culture medium also completely ablated both the PGE2- and forskolin-induced increases in PDE activity (FIG. 3B), whereas neither actinomycin D nor cycloheximide alone significantly affected basal PDE activity (data not shown). Finally, extended studies demonstrated that the stimulatory effects of PGE2 and forskolin on PDE activity were also abrogated by co-incubating the ASM cells with the putative selective PKA inhibitor, H89 (10 µM), whereas cells treated with H89 alone showed no significant change in basal PDE activity (FIG. 3C). Taken together, these data are consistent with the notion that heterologous β2AR desensitization in ASM cells, resulting from prolonged exposure to PGE2 or forskolin, evokes upregulated PDE4 activity that is due to PKA-dependent de novo mRNA and protein synthesis.

Role of PKA in Regulating PDE4D5 Expression in PGE2-Exposed ASM Cells.

Given recent evidence demonstrating that PDE4D5 is the functionally dominant cAMP-regulating PDE4 isoform in cultured human ASM cells (5), examination of whether heterologous β2AR desensitization in ASM cells evokes altered expression of PDE4D5 transcripts was undertaken. Confluent cultures of ASM cells exposed to PGE2 (100 nM×24 hr) exhibited time-dependent increases in PDE4D5 mRNA expression, with peak induction detected at 6 hr and sustained upregulated expression observed for up to 24 hr (FIG. 4A). Densitometric analysis of the temporal changes in PDE4D5 mRNA expression examined in 3 separate experiments demonstrated that peak expression averaged 5.9-fold above that detected in unstimulated cells. Since PDE4D5 expression in ASM cells was previously shown to be regulated by a CRE-containing promoter (30), examination of the effects of PGE2 on cAMP/PKA-dependent downstream signaling events coupled to CRE activation was performed. As shown in FIG. 4B, ASM cells treated with PGE2 (100 nM) exhibited transiently increased phosphorylation of the CRE-binding transcription co-factors, CREB and ATF1, which peaked at 30 min and was subsequently ablated by 180 min. To determine the role of PKA in mediating the latter response to PGE2, the effects of knockdown of PKA expression using siRNA duplexes directed against the human PKAα and PKAγ catalytic subunits was assessed. Preliminary experiments (n=3) demonstrated that Lipofectamine transfection of the PKA siRNA duplexes produced maximal knockdown of PKAα protein levels at 72 hr post-transfection that ranged between ~70-90%. Accordingly, confluent cultures of ASM cells were initially treated for 72 hr with either vehicle alone, a scrambled siRNA sequence serving as control, or the siRNA duplexes directed against the PKA catalytic subunits. Cells were then examined for induced expression of phosphorylated CREB/ATF1 proteins at 30 min following exposure to PGE2 (100 nM). As depicted in FIG. 4C, in the absence of PGE2, basal levels of phosphorylated CREB/ATF1 protein expression were little affected by transfection with either the scrambled RNA (scRNA; lane 3) or PKA siRNA (lane 5) preparations. Conversely, the PGE2-induced upregulated expression of phosphorylated CREB/ATF1 (lane 2) was distinctly inhibited in cells transfected with siRNAs directed against PKA (lane 6), whereas the scrambled siRNA sequence had no effect (lane 4). Thus, in concert with above observations implicating PKA activation in mediating the upregulated PDE4 activity in PGE2-exposed ASM cells, these data demonstrate that PKA activation is intimately involved in regulating PGE2-induced CREB/ATF1 phosphorylation associated with upregulated PDE4D5 expression.

PKA-Mediated Regulation of ERK1/2 Activation in PGE2-Exposed ASM Cells.

Figure 5:
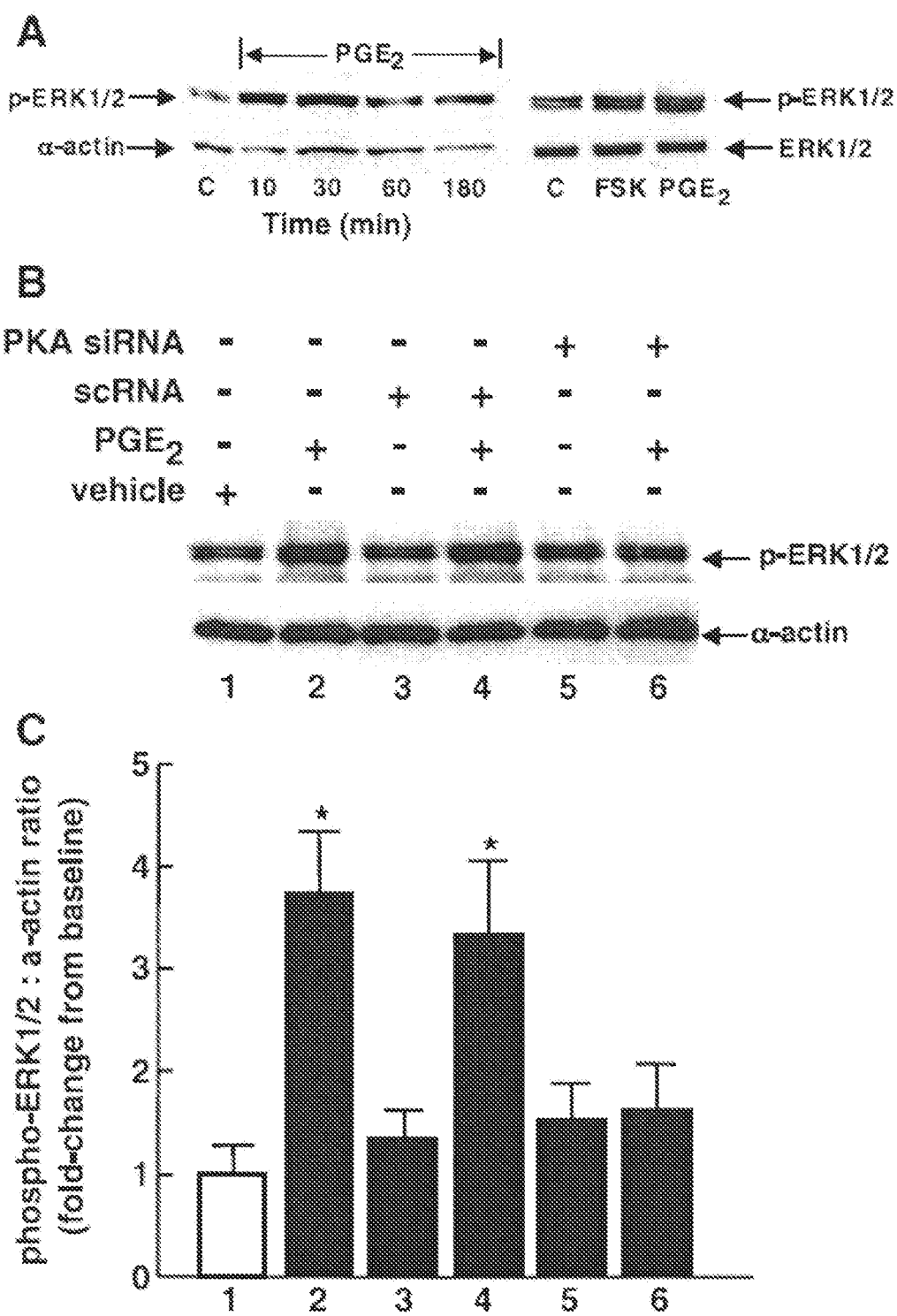
FIG. 5. $PGE_2$ elicits PKA-dependent activation of ERK1/2 in ASM cells. (A) Western blot depicting acute $PGE_2$- and forskolin-induced phosphorylation of ERK1/2. (B) $PGE_2$-induced phosphorylation of ERK1/2 is prevented in ASM cells that are transfected with siRNA duplexes directed against the PKAα and PKAβ catalytic subunits, whereas transfection with a scrambled (control) siRNA duplex (scRNA) has no effect. (C) Quantitative analysis of the effects of PKA siRNA transfection on $PGE_2$-induced ERK1/2 phosphorylation. Relative to untreated control cells, the mean±SE value of the densitometric ratios of phosphorylated ERK1/2-to-α-actin is significantly increased in $PGE_2$-exposed ASM cells. Contrasting the lack of effect seen in ASM cells transfected with the scRNA preparation, the $PGE_2$-induced increase in ERK1/2 phosphorylation is prevented in cells that are transfected with the PKA siRNA duplexes. Data are mean±SE values from 4 experiments (*$p<0.05$).

Apart from its activation by the cAMP/PKA pathway, CREB can also be activated via other signaling events, notably including ERK1/2 activation (23). Moreover, in this context, cross-talk between the cAMP/PKA and ERK1/2 signaling pathways has also been demonstrated wherein PKA can activate the Ras/c-Raf1/MEK1/2 and/or the Rap1/B-Raf/MEK1/2 signaling pathway, leading to downstream activation of ERK1/2 (29) which, in turn, can mediate CREB phosphorylation via activation of the CREB kinases, p90RSK or MSK-1 (23). Given this evidence, together with recent reports implicating a critical role for ERK1/2 activation in mediating the hyporesponsiveness of ASM to β2AR stimulation under different pro-asthmatic conditions (14, 28, 38), next the potential regulatory interplay between PKA and ERK1/2 signaling in PGE2-exposed ASM cells was examined. Initial studies demonstrated that, relative to unstimulated control cells, ASM cells exposed to PGE2 (100 nM) exhibited increased expression of phosphorylated ERK1/2, with peak phosphorylation detected at 30 min, followed by sustained enhanced phosphorylation for at least up to 180 min (FIG. 5A; left). As with $PGE_2$, forskolin (100 nM) was also found to elicit ERK1/2 phosphorylation (FIG. 5A; right). In subsequently evaluating the potential role of PKA in mediating the $PGE_2$-induced activation of ERK1/2, ASM cells were first treated for 72 hr with vehicle alone or with either scrambled RNA or siRNAs directed against the PKA catalytic subunits, and then examined for induced phosphorylation of ERK1/2 at 30 min following exposure to $PGE_2$. As shown in FIG. 5B, relative to vehicle-treated control cells (lane 1), ERK1/2 phosphorylation was markedly increased in $PGE_2$-treated cells (lane 2) and, while cells pretreated with either the scrambled or PKA siRNAs alone showed little change in ERK1/2 phosphorylation (lanes 3 and 5, respectively), the $PGE_2$-induced upregulation of ERK1/2 phosphorylation was distinctly inhibited in ASM cells that were pretreated with the PKA siRNAs (lane 6), whereas pretreatment of the PGE-exposed cells with scrambled RNA had no appreciable effect (lane 4). Analysis of the results obtained in 4 experiments is depicted in FIG. 5C, wherein the levels of ERK1/2 phosphorylation detected under the different experimental conditions are displayed as the mean±SE values of the fold-changes in the densitometric ratios of phosphorylated ERK1/2-to-α-actin. It will be noted that the $PGE_2$-induced increase in ERK1/2 phosphorylation amounted to 3.76±0.64-fold above that detected in control (vehicle-treated) cells ($p<0.05$) and, in contrast to the lack of effect of scRNA, the $PGE_2$-induced phosphorylation of ERK1/2 was inhibited in cells transfected with PKA siRNA. Thus, these data demonstrate that the induction of ERK1/2 activation in $PGE_2$-exposed ASM cells is regulated by PKA, as further examined below.

Role of PKA- and ERK1/2-Coupled Signaling in Regulating CREB/ATF1 Activation and PDE4D5 Expression in PGE2-Exposed ASM Cells.

Figure 6:
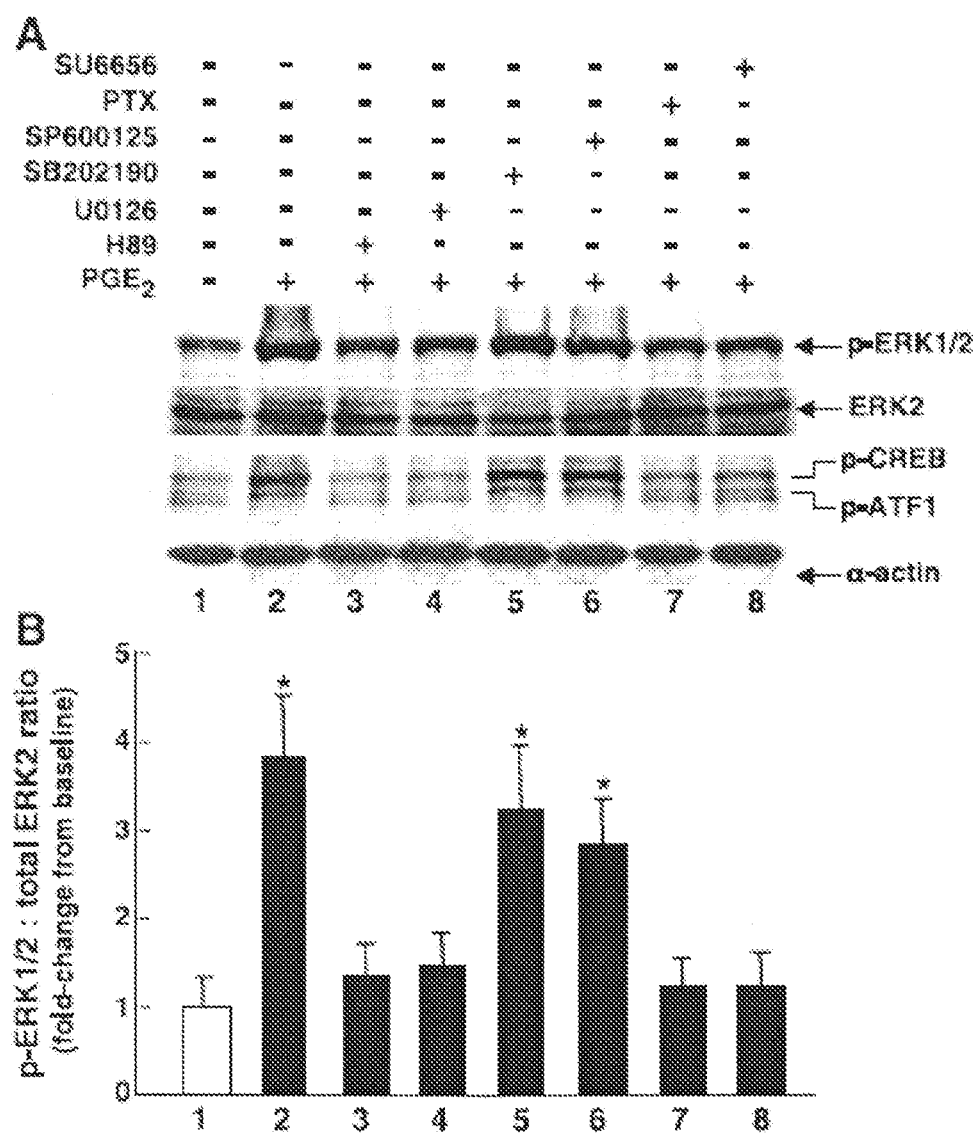
FIG. 6. PGE2-induced activation of the PKA and ERK1/2 signaling pathways mediates upregulated expression of PDE4D5 transcripts in ASM cells. (A) Western blots depicting that PGE2-induced phosphorylation of ERK1/2 and CREB/ATF1 proteins is ablated in ASM cells pretreated with inhibitors of either PKA (H89), MEK-ERK1/2 (U1026), or Src tyrosine kinase (SU6656), or by ADP ribosylation of Gi protein with pertussis toxin (PTX). (B) PGE2-induced upregulated expression of PDE4D5 mRNA transcripts is also ablated in ASM cells pretreated with either of the latter inhibitors.

Small molecule inhibitors were next employed to further identify the signaling mechanisms involved in regulating ERK1/2 and CREB/ATF1 activation, as well as PDE4D5 mRNA expression in PGE2-exposed ASM cells. In these studies, induced changes in expression of phosphorylated ERK1/2 and CREB/ATF proteins were detected by Western blot analysis following treatment of ASM cells for 30 min with vehicle alone (control) or 100 nM PGE2, both in the absence and presence of pretreatment with previously reported maximal effective concentrations of specific inhibitors. As depicted in FIG. 6A, relative to controls (lane 1), cells treated with PGE2 exhibited increased expression of both phosphorylated ERK1/2 and CREB/ATF proteins (lane 2), and these effects were abrogated in PGE2-exposed cells that were pretreated with either the PKA inhibitor, H89 (10 µM;

lane 3), or the MEK-ERK1/2 inhibitor, U0126 (5 µM; lane 4). By contrast, neither PGE2-induced phosphorylation of ERK1/2 nor CREB/ATF was affected in cells pretreated either with the p38 MAPK inhibitor, SB202190 (10 µM; lane 5), or the JNK inhibitor, SP600125 (10 µM; lane 6). Of significance, PGE2-induced up-regulated expression of phosphorylated ERK1/2 and CREB/ATF proteins was also largely prevented in cells that were pretreated with pertussis toxin (PTX; 100 ng/ml) (lane 7), which ADP ribosylates Gi protein, or with the Src family tyrosine kinase inhibitor, SU6656 (10 µM; lane 8).

The above inhibitors were also examined with respect to their modulatory effects on the upregulated expression of PDE4D5 mRNA in PGE2-exposed ASM cells. PDE4D5 transcripts were detected by RT-PCR following exposure of ASM cells for 6 hr to vehicle alone (control) or 100 nM PGE2, both in the absence and presence of pretreatment with either inhibitor. In concert with their effects on PGE2-induced expression of phosphorylated ERK1/2 and CREB/ATF, the inhibitors exerted comparable modulatory effects on PGE2-induced upregulated expression of PDE4D5 transcripts. Accordingly, as shown in FIG. 6B, relative to control cells (lane 1), the induced upregulated expression of PDE4D5 mRNA in PGE2-exposed ASM cells (lane 2) was largely prevented by pretreating the cells with either H89 (lane 3) or the MEK/ERK1/2 inhibitor (lane 4). Moreover, whereas neither the p38 MAPK nor JNK inhibitor (lanes 5 and 6, respectively) had an attenuating effect, the PGE2-induced upregulated expression of PDE4D5 transcripts was markedly inhibited by pretreating the cells either with PTX (lane 7) or the Src inhibitor (lane 8). Thus, when taken together, these observations support the notion that PGE2-induced expression of PDE4D5 transcripts in ASM cells is regulated by PKA-dependent activation of ERK1/2 that, in turn, serves to activate CREB/ATF proteins and, thereby, initiate PDE4D5 transcription.

Mechanism of PKA-Dependent Activation of ERK1/2 in PGE2-Exposed ASM Cells: Role of Altered G Protein-Coupled Signaling.

It is well documented that PKA can activate ERK1/2 either via Gs-coupled or Gi-βγ subunit-mediated stimulation of Src-induced signaling via the Rap1/B-Raf/MEK1/2 or the Ras/c-Raf1/MEK1/2 pathway, respectively (29). Moreover, cAMP-elevating agents can also activate ERK1/2 via a direct stimulatory effect of cAMP on EPAC (exchange protein directly activated by cAMP) proteins which, in turn, can initiate sequential downstream signaling via the Rap1/B-Raf/MEK1/2 pathway (29). To distinguish the relative contributions of these downstream signaling pathways, the effects of selective inhibitors of c-Raf1 and Rap1 on PGE2-induced ERK1/2 phosphorylation in ASM cells was examined. As shown in FIG. 7A, relative to control (untreated) cells (lane 1), ASM cells exposed for 30 min to PGE2 exhibited increased expression of phosphorylated ERK1/2 (lane 2) and, as expected, this effect was completely abrogated by pretreating the cells with the selective MEK1/2 inhibitor, U0126 (lane 3). Comparably, pretreatment with the selective c-Raf1 inhibitor, GW5074 (20 µM), also completely ablated the stimulatory effect of PGE2 on phosphorylated ERK1/2 expression (lane 4), whereas cells pretreated with GGTI-298 (25 µM), a potent and selective inhibitor of Rap1 activation (27), did not exhibit attenuated PGE2-induced ERK1/2 phosphorylation (lane 5). Thus, these data implicate downstream Raf1-coupled signaling in mediating ERK1/2 activation in PGE2-exposed ASM cells, supporting the notion that the observed PKA-dependent activation of ERK1/2 is likely attributed to Gi-βγ-mediated Src signaling via the Ras/c-Raf1/MEK1/2 pathway. The latter possibility was directly addressed in extended experiments wherein the effects of PGE2 on ERK1/2 activation in ASM cells at 24 hr following their transfection was examined either with an adenovirus vector expressing lacZ (adeno-LacZ), serving as a negative control, or with adeno-βARK-ct, which encodes the βARK1 carboxyl-terminal domain that blocks Gβγ signaling (25,26), both at a multiplicity of infection (MOI) of 100. As shown in FIG. 7B, cells transfected with adeno-LacZ exhibited distinct PGE2-induced ERK1/2 phosphorylation (lane 2), whereas this response to PGE2 was completely ablated in cells transfected with adeno-βARK-ct (lane 4). Thus, together with the above observations, these data support the concept that activation of ERK1/2 in PGE2-exposed ASM cells is attributed to PKA-dependent activation of Gi-βγ-mediated signaling via the Ras/c-Raf1/MEK1/2 pathway.

PKA-Dependent ERK1/2 Signaling Regulates PDE4 Activity and Constrictor and Relaxation Responsiveness in β2AR-Desensitized ASM.

Figure 8:
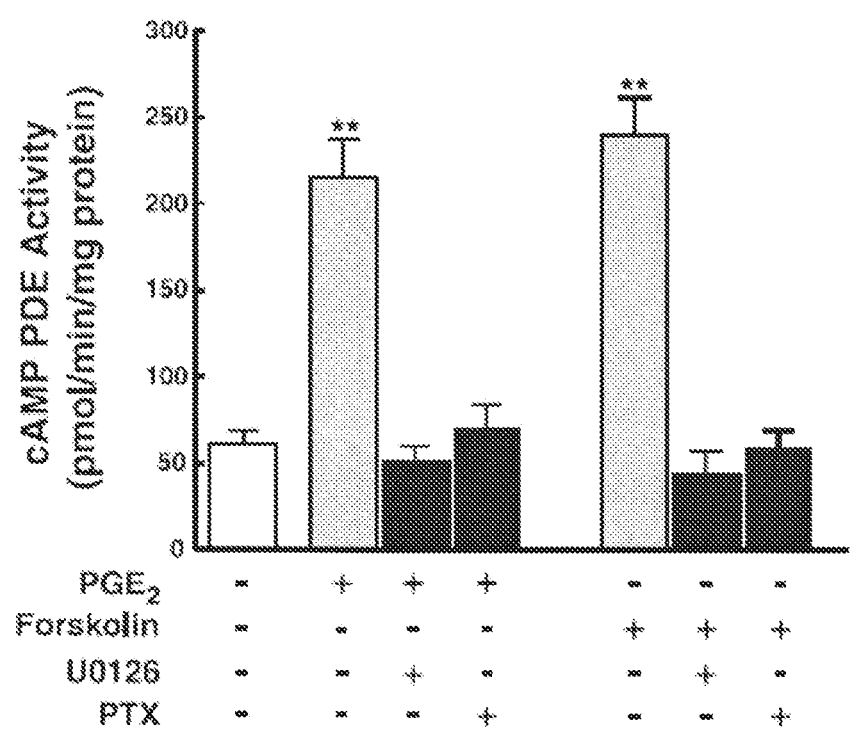
FIG. 8. Gi protein and ERK1/2 activation mediate upregulated PDE activity in PGE2- and forskolin-treated ASM cells. PDE4 activity is significantly increased in ASM cells exposed for 24 hr to 100 nM of PGE2 or forskolin. Stimulation of PDE activity is ablated in PGE2- and forskolin-exposed ASM cells by pretreatment with the ERK1/2 inhibitor, U0126, or by ADP ribosylation of Gi protein with PTX. Data represent mean±SE values based on 4 measurements obtained under each treatment condition. **$p<0.01$.
Figure 9:
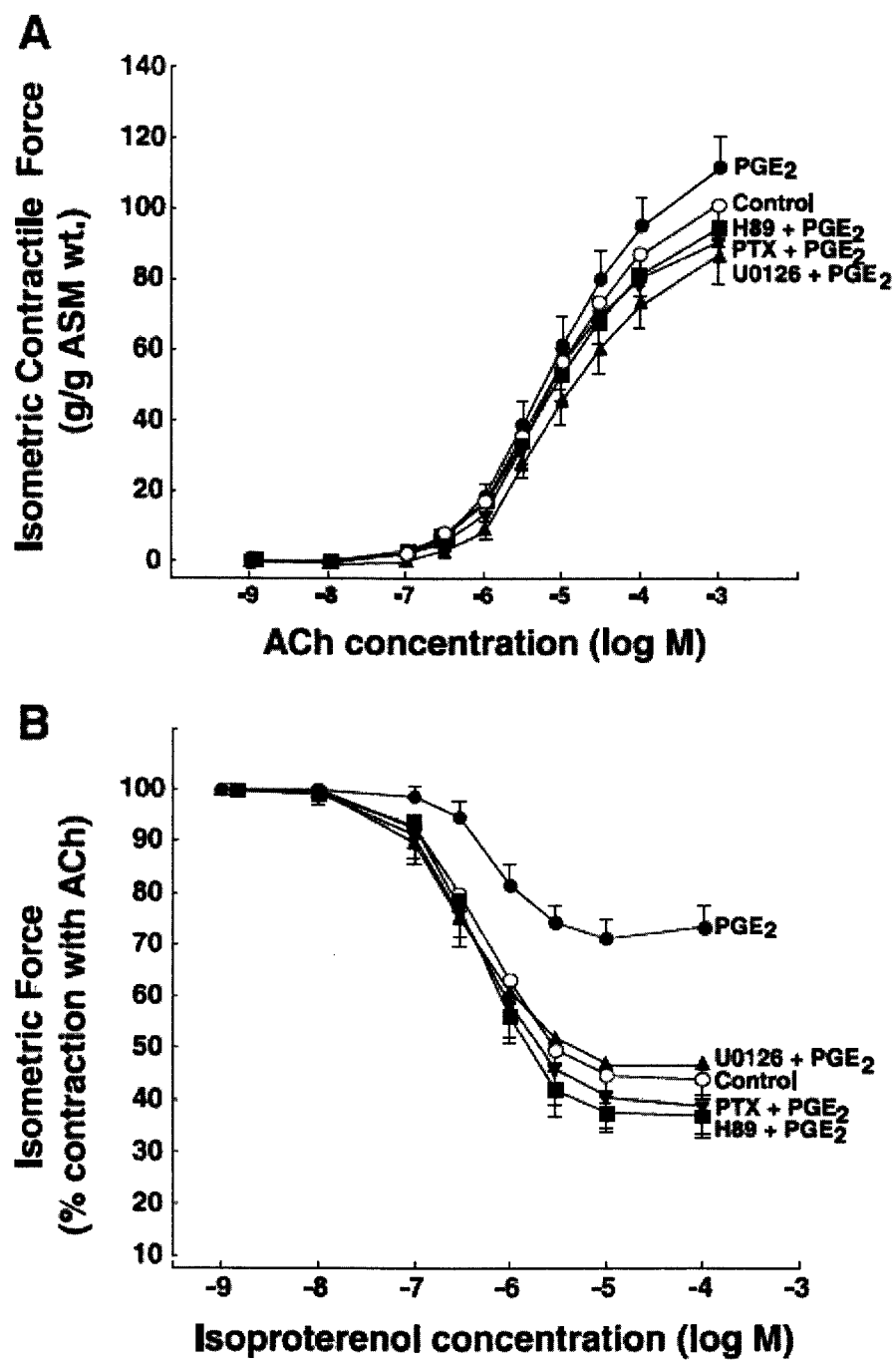
FIG. 9. Changes in ASM constrictor and relaxation responsiveness accompanying PGE2-induced heterologous β2AR desensitization are mediated by activation of the PKA and ERK1/2 signaling pathways. Relative to vehicle-treated controls, rabbit ASM tissues exposed for 24 hr to PGE2 (100 nM) exhibit significantly increased constrictor responses to ACh (A) and impaired relaxation responses to isoproterenol (B). The PGE2-induced changes in ASM constrictor and relaxation responsiveness are abrogated in tissues that are pretreated with inhibitors of either PKA (H89) or MEK1/2 (U1026), or by ADP ribosylation of Gi protein with PTX. Data represent mean±SE values from 4 paired experiments.

To ascertain the physiological implications of the above mechanism of interplay between the cAMP/PKA and c-Raf1/MEK/ERK1/2 signaling pathways in the β2AR-desensitized state, the independent effects of inhibition of PKA, Gi protein, and ERK1/2 function on the changes in PDE activity and constrictor and relaxation responsiveness in human ASM cells and rabbit tissues was examined, respectively, accompanying heterologous β2AR desensitization. As demonstrated in FIG. 8, relative to control (vehicle-treated) ASM cells, cAMP PDE activity was significantly increased in cells that were incubated for 24 hr with 100 µM of PGE2 or forskolin, and this induced stimulation of PDE4 activity was completely ablated in both PGE2- and forskolin-exposed cells that were pretreated with either the MEK1/2 inhibitor, U1026 (5 µM), or PTX (100 ng/ml). Comparably, as depicted in FIG. 9, relative to the responses obtained in control rabbit ASM tissues, the significantly increased constrictor responses to ACh (FIG. 9A) and impaired relaxation responses to isoproterenol (FIG. 9B) detected in PGE2-exposed ASM tissues were abrogated by pretreating these tissues with either PTX or U1026, or with the PKA inhibitor, H89. In relation to these observations, it should be noted that in separate studies wherein vehicle-exposed control ASM tissues were comparably pretreated with each of the latter inhibitors, there was no significant effect of either agent on the tissues' constrictor or relaxation responses (data not shown). Thus, these data provide physiological evidence supporting the notion that the above mechanism of PGE2-induced cross-talk between the cAMP/PKA and ERK1/2 signaling pathways mediates the rolipram-sensitive changes in PDE activity and ASM constrictor and relaxation responsiveness exhibited in the β2AR-desensitized state.

EXAMPLE II

Homologous β2-Adrenergic Receptor Desensitization in Airway Smooth Muscle: Role of Phosphodiesterase 4

Role of PDE4 in Regulating cAMP Responses in ASM Cells Following Prolonged Homologous β2AR Desensitization.

Figure 10:
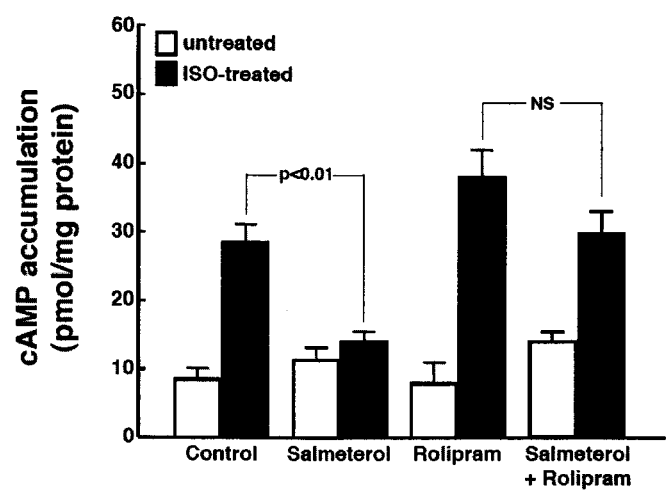
FIG. 10. Inhibition of PDE4 prevents the induction of impaired β2AR-mediated cAMP accumulation accompanying homologous β2AR desensitization with the long-acting β2AR agonist, salmeterol, in cultured human ASM cells. In contrast to vehicle-exposed (control) ASM cells, acute isoproterenol (ISO; 1.0 μM)-induced cAMP accumulation is markedly attenuated in salmeterol-exposed cells ($p<0.01$). By comparison, in ASM cells pretreated with rolipram (10 μM), the cAMP responses to isoproterenol are increased and unaltered by pre-exposing the cells to salmeterol. Data represent mean±SE values from paired 3 experiments.

Upregulated PDE4 activity has been implicated in mediating heterologous β2AR desensitization in ASM following its prolonged exposure to receptor- and non-receptor-coupled cAMP elevating agents. See Example I. To determine the role of PDE4 activity in mediating homologous β2AR desensitization in ASM, the acute changes in intracellular cAMP accumulation detected at 5 min following administration of a near half-maximal effective concentration of isoproterenol (ISO; 1.0 µM) following prolonged exposure of cultured human ASM cells to either vehicle alone or to a maximally effective concentration of the long-acting β2AR agonist, salmeterol (10 µM×24 hr), both in the absence and presence of co-treatment with the PDE4-selective inhibitor, rolipram (10 µM) was examined. As shown in FIG. 10, relative to vehicle-exposed (control) cells, in the absence of rolipram, salmeterol-exposed ASM cells exhibited homologous β2AR desensitization, as evidenced by significantly reduced cAMP responses to ISO. By comparison, ASM cells pretreated with rolipram exhibited slightly increased ISO-induced cAMP accumulation, and the response to ISO was largely preserved in salmeterol-exposed cells that were co-treated with rolipram. Thus, these observations implicate PDE4 activity in mediating the impaired isoproterenol-induced accumulation of cAMP that accompanies prolonged homologous β2AR desensitization in human ASM cells.

Regulation of cAMP PDE Activity in Homologous β2AR-Desensitized ASM Cells.

Figure 11:
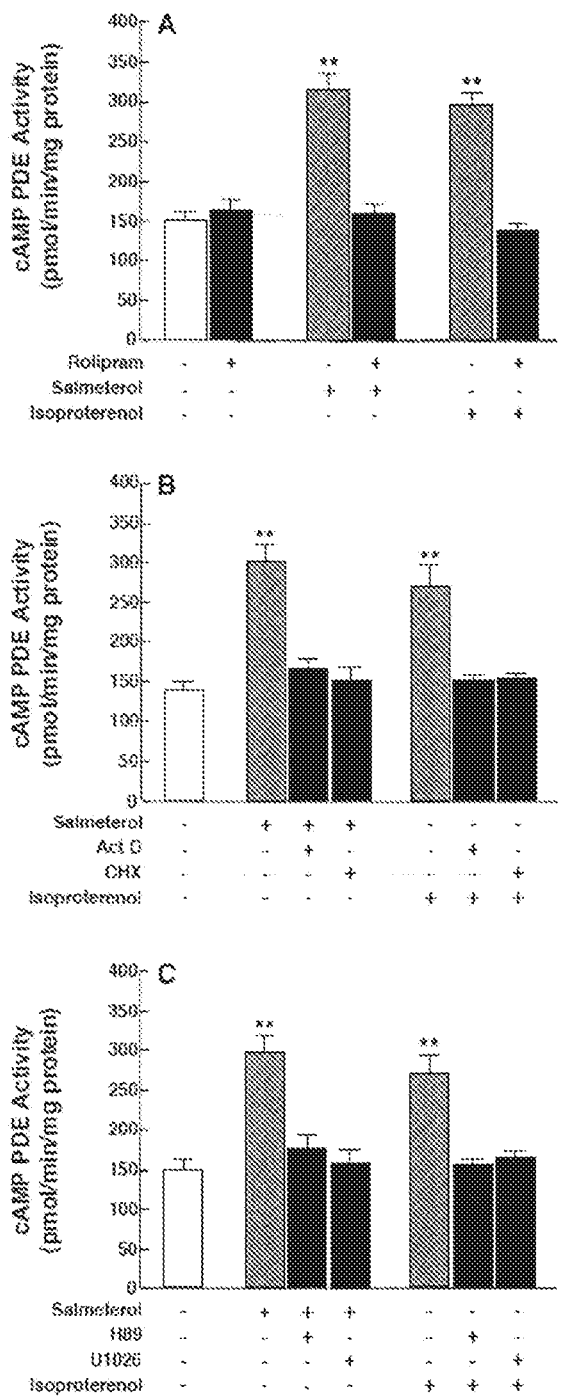
FIG. 11. Regulation of cAMP PDE4 activity in cultured human ASM cells following prolonged exposure to β2AR agonists. Relative to vehicle-treated (control) ASM cells, levels of cAMP activity are significantly increased in cells exposed for 24 hr to 10 μM of either salmeterol or isoproterenol. The stimulated PDE activity is ablated in β2AR agonist-exposed ASM cells by pre-treatment either with the PDE4 inhibitor, rolipram (A), the transcription or protein synthesis inhibitors, actinomycin D (Act D) and cycloheximide (CHX), respectively (B), the PKA inhibitor, H89, or the ERK1/2 inhibitor, U0126 (C). Data represent mean±SE values based on 3-4 determinations made under each treatment condition. **$p<0.01$.

To elucidate the mechanism underlying the above rolipram-sensitive effects of homologous β2AR desensitization, the changes in total cAMP PDE activity and the effects of pre-treatment with selective small molecule inhibitors on this activity were examined in cultured ASM cells following their prolonged exposure to a β2AR agonist. Relative to the mean (±SE) basal level of PDE activity detected in vehicle-treated (control) cells (i.e., 150.2±11.1 pmol/min/mg protein), ASM cells incubated for 24 hr with a maximally effective concentration (10 µM) of either salmeterol or isoproterenol exhibited significantly increased levels of PDE activity that averaged ~2-fold above control (FIG. 11A). The stimulatory effect of prolonged exposure to salmeterol or isoproterenol on PDE activity was completely abrogated in cells that were pretreated with rolipram (10 µM), implying that the upregulated cAMP-PDE activity exhibited by the β2AR-desensitized cells was attributed to PDE4 activity. In separate experiments, pretreatment of cells with the transcriptional inhibitor, actinomycin D (4 µM), or with the protein synthesis inhibitor, cycloheximide (100 µM), also completely ablated the increase in PDE activity elicited by prolonged exposure to the β2AR agonists (FIG. 11B), whereas neither actinomycin D nor cycloheximide alone significantly affected basal PDE activity (data not shown). Finally, extended studies demonstrated that pre-treatment with either the selective PKA inhibitor, H89 (10 µM), or the MEK-ERK1/2 inhibitor, U0126 (5 µM), prevented the stimulatory effects of salmeterol and isoproterenol on PDE activity (FIG. 11C), whereas neither H89 nor U0126 alone had a significant effect on basal PDE activity (data not shown). Collectively, these data are consistent with the notion that homologous β2AR desensitization in ASM cells resulting from prolonged exposure to a β2AR agonist elicits upregulated PDE4 activity that is attributed to PKA- and ERK1/2-dependent de novo mRNA and protein synthesis.

Role of PDE4 in Regulating Constrictor and Relaxation Responsiveness in ASM Tissues Following Prolonged Homologous β2AR Desensitization.

Figure 12:
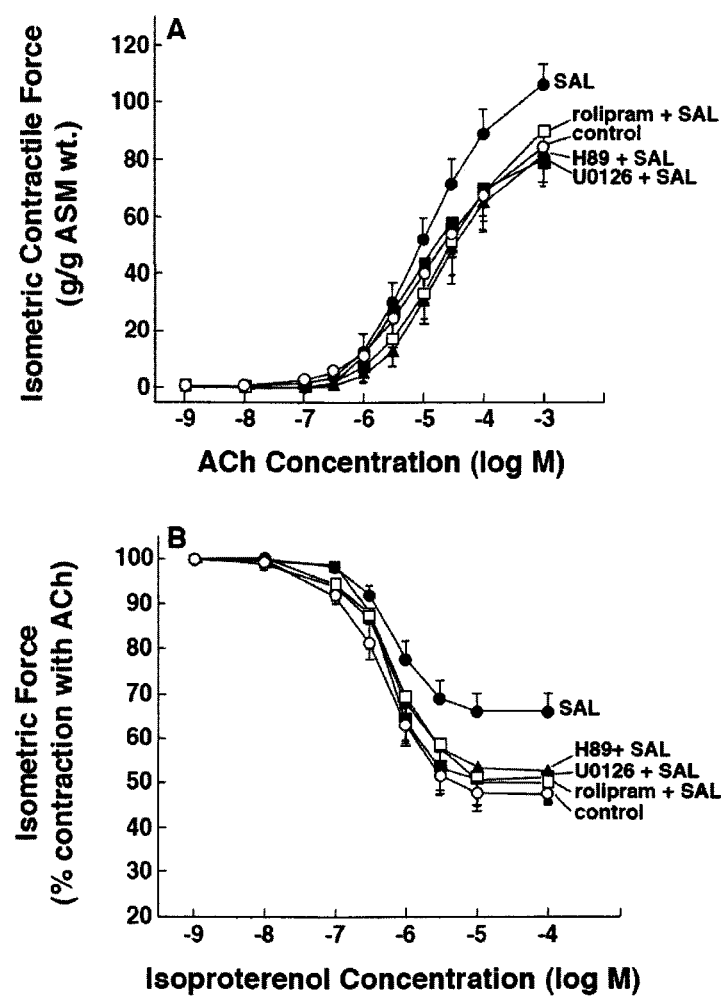
FIG. 12. Inhibition of PDE4 or the PKA and ERK signaling pathways prevents the induction of altered ASM tissue constrictor and relaxation responsiveness accompanying prolonged homologous β2AR desensitization. Relative to vehicle-treated controls, rabbit ASM tissues exposed for 24 hr to salmeterol (10 μM) exhibit significantly increased constrictor responses to ACh (A) and impaired relaxation responses to isoproterenol (B). Pre-treatment with the PDE4-selective inhibitor, rolipram (10 μM), the PKA inhibitor, H89 (10 μM) or the ERK1/2 inhibitor, U0126 (5 μM) prevents the salmeterol-induced changes in ASM constrictor and relaxation responsiveness. Data represent mean±SE values from 6-8 paired experiments.

In light of the above observations, the regulatory role of PDE4 activity and the contributions of PKA and ERK1/2 signaling in mediating the effects of prolonged homologous β2AR desensitization on ASM function were subsequently examined. In these studies, constrictor responses to ACh and relaxation responses to isoproterenol were compared in isolated rabbit ASM tissues that were exposed for 24 hr to either vehicle alone (control) or a pre-determined maximally effective concentration of salmeterol (10 µM), both in the absence and presence of pretreatment with either rolipram (10 µM), H89 (10 µM), or U0126 (5 µM). Relative to their respective vehicle-treated controls, ASM tissues exposed to salmeterol (SAL) exhibited significantly increased constrictor responsiveness to exogenously administered ACh (FIG. 12A), yielding a mean±SE maximal constrictor response (Tmax) value of 106.2±8.9 g/g ASM wt. vs. the value of 84.3±7.1 g/g ASM wt. obtained in the control tissues (p<0.05). This enhanced constrictor responsiveness to ACh was completely abrogated in SAL-exposed tissues that were pretreated either with rolipram, H89, or U0126. Under the same treatment conditions, during subsequent sustained half-maximal contraction of the tissues with ACh, cumulative administration of isoproterenol produced dose-dependent relaxation of the pre-constricted ASM segments. Relative to control tissues, the relaxation responses to isoproterenol were significantly attenuated in the SAL-exposed ASM segments (FIG. 12B), consistent with their development of homologous β2AR desensitization. Accordingly, the mean±SE maximal relaxation (Rmax) response in the SAL-exposed tissues amounted to 33.39±5.1% vs. the average Rmax value of 52.3±4.9% obtained in the control ASM segments (p<0.01). This impaired relaxant responsiveness to isoproterenol was also completely ablated in SAL-exposed tissues that were pre-treated either with rolipram, H89, or U0126. Contrasting these observations in SAL-exposed tissues, ASM tissues that were comparably treated for 24 hr with rolipram, H89, or U0126 alone did not exhibit any significant changes in either their constrictor responses to ACh or relaxation responses to isoproterenol (data not shown). Taken together, these observations implicate a key regulatory role for PDE4 activity that is coupled to PKA and ERK1/2 activation in mediating the pro-asthmatic-like changes in ASM constrictor and relaxation responsiveness that are elicited by prolonged homologous β2AR desensitization.

Regulation of PDE4D5 Expression by PKA and ERK1/2 in Homologous β2AR-Desensitized ASM.

Figure 13:
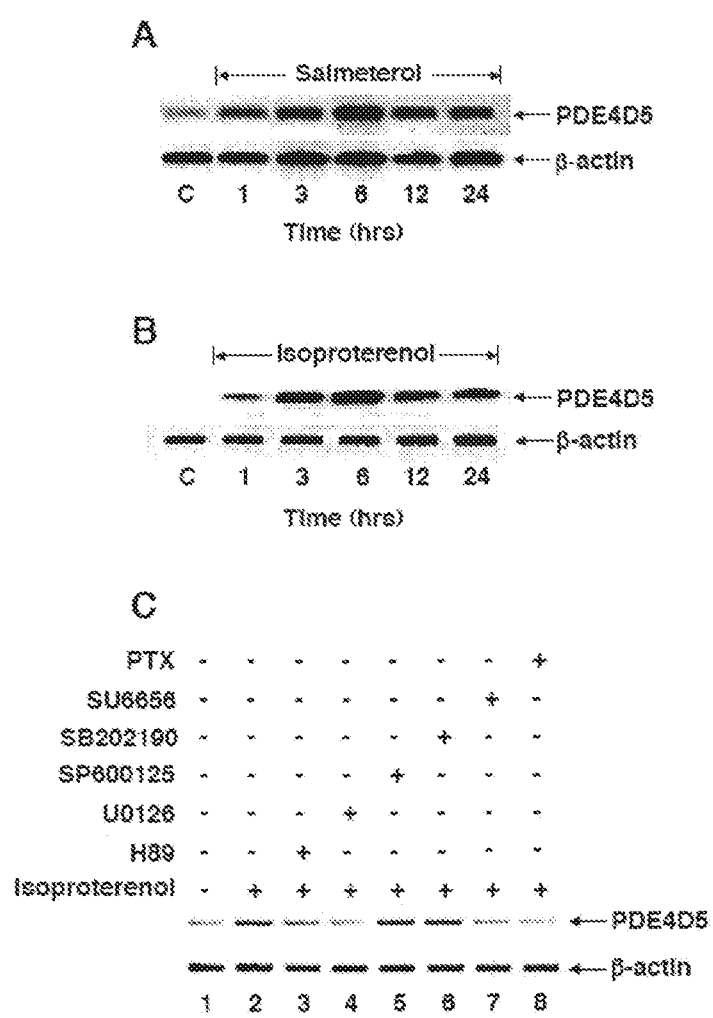
FIG. 13. Regulation of PDE4D5 mRNA expression in β2AR agonist-exposed ASM cells. ASM cells treated with salmeterol (10 μM) (A) or isoproterenol (10 μM) (B) exhibit temporal increases in PDE4D5 mRNA expression, with peak expression of transcripts detected at 6 hr. (C) β2AR agonist-induced upregulated expression of PDE4D5 mRNA transcripts is ablated in ASM cells pretreated with inhibitors of PKA (H89), MEK-ERK1/2 (U1026), Src tyrosine kinase (SU6656), or by ADP ribosylation of Gi protein with PTX, whereas pre-treatment with the JNK inhibitor (SP600125) or the p38 MAPK inhibitor (SB202190) has no effect.

Based on the above observations, together with recent evidence that identifies PDE4D5 as the functionally dominant cAMP-regulating PDE4 isoform in cultured human ASM cells (5), next a series of experiments was conducted that were aimed at identifying the effects of prolonged β2AR agonist exposure on ASM expression of PDE4D5 mRNA transcripts and the roles played by the PKA and MAPK signaling pathways in regulating β2AR agonist-induced changes in PDE4D5 expression. Initial studies demonstrated that ASM cell cultures exposed for 24 hr to 10 µM of either salmeterol (FIG. 13A) or isoproterenol (FIG. 13B) exhibited time-dependent increases in PDE4D5 mRNA expression, with peak induction of PDE4D5 transcripts by either agonist observed at 6 hr and sustained upregulated expression detected for up to 24 hr. Densitometric analysis of the temporal changes in mRNA expression examined in 3 paired experiments demonstrated that peak induction of PDE4D5 transcripts elicited by salmeterol and isoproterenol averaged 7.3- and 5.7-fold above that detected in unstimulated cells, respectively. Small molecule inhibitors were subsequently employed to identify the roles of PKA and MAPK signaling in regulating the induction of PDE4D5 expression. As demonstrated in one of three representative experiments in FIG. 13C, relative to vehicle-exposed (control) cells (lane 1), the induced upregulated expression of PDE4D5 mRNA transcripts detected at 6 hr following exposure of ASM cells to 10 µM isoproterenol (lane 2) was largely prevented by pretreating the cells with either the PKA inhibitor, H89 (lane 3), or the MEK/ERK1/2 inhibitor, U0126 (lane 4). Conversely, isoproterenol-induced upregulation of PDE4D5 mRNA was unaffected in cells pretreated with previously reported maximal effective concentrations of either the specific JNK inhibitor, SP600125 (10 µM; lane 5), or the p38 MAPK inhibitor, SB202190 (10 µM; lane 6), whereas the induction of PDE4D5 transcripts was prevented in isoproterenol-exposed cells that were pretreated with the Src family tyrosine kinase inhibitor, SU6656 (10 µM; lane 7), or pertussis toxin (PTX; 100 ng/ml) (lane 8), which ADP ribosylates Gi protein. The latter observations are consistent with the known role of Gi protein-mediated activation of Src in eliciting ERK1/2 activation in other cell types (see below) and, when taken together, the above results support the concept that β2AR agonist-induced upexpression of PDE4D5 transcripts in ASM cells is regulated by Gi protein/Src-coupled interaction between the PKA and ERK1/2 signaling pathways. Studies were next pursued to examine the nature of the suspected interplay between these signaling pathways, as described below.

PKA-Dependent Regulation of CREB and ERK1/2 Activation in β2AR Agonist-Exposed ASM.

Figure 14:
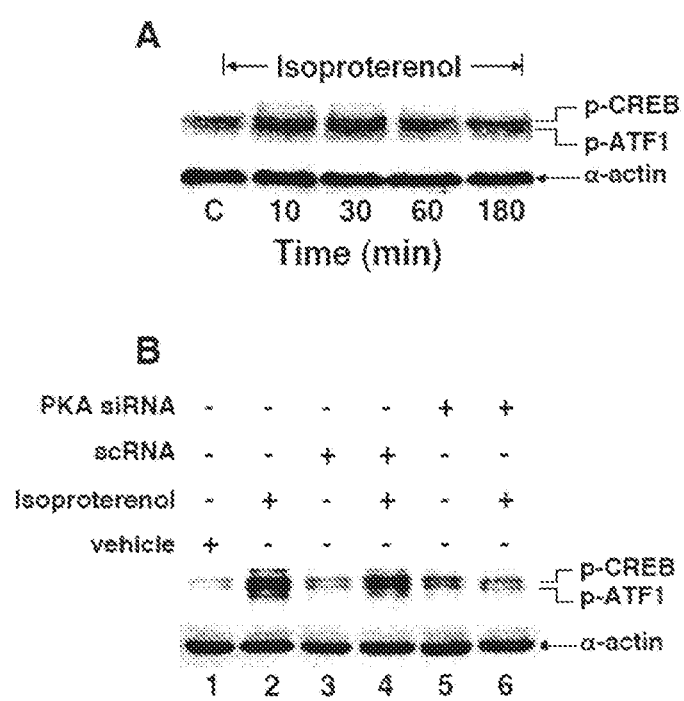
FIG. 14. β2AR agonist-exposed ASM cells exhibit PKA-dependent activation of the CRE-regulating transcription co-factors, CREB and ATF1. (A) Western blot depicting that β2AR stimulation elicits transiently upregulated expression of phosphorylated CREB and ATF1 proteins in ASM cells, with peak phosphorylation detected at 30 min. (B) β2AR agonist-induced phosphorylation of CREB/ATF1 is prevented in ASM cells transfected with siRNA duplexes directed against the PKAα and PKAγ catalytic subunits, whereas transfection with a scrambled (control) siRNA duplex (scRNA) has no effect.

Because PDE4D5 transcription in ASM cells is regulated by a CRE-containing promoter (30), the effects of β2AR stimulation on cAMP/PKA-dependent downstream signaling events coupled to CRE activation was examined. As exemplified by a representative immunoblot (i.e., 1 of 3 experiments) in FIG. 14A, ASM cells treated with isoproterenol (10 µM) exhibited transiently increased phosphorylation of the CRE-binding transcription co-factors, CREB and ATF1, which peaked at 30 min and was subsequently largely abrogated by 180 min. Qualitatively similar temporal changes in CREB/ATF1 phosphorylation were also detected in ASM cells that were exposed to 10 nM salmeterol (data not shown). To ascertain whether the stimulatory effect of β2AR agonist exposure on CREB/ATF1 phosphorylation was due to PKA activation, the effects of isoproterenol on CREB/ATF1 phosphorylation in vehicle-exposed ASM cells and in cells wherein PKA expression was suppressed by transfection with siRNA duplexes directed against the human PKAα and PKAα catalytic subunits was compared. It has been previously demonstrated that Lipofectamine transfection of ASM cells with these PKA siRNA duplexes produced maximal knockdown of PKAα protein levels at 72 hr post-transfection that ranged between ~70-90%. See Example I. Accordingly, confluent cultures of ASM cells were initially treated for 72 hr with either vehicle alone, a scrambled siRNA sequence serving as a negative control, or the siRNA duplexes directed against the PKA catalytic subunits. Cells were then examined for induced expression of phosphorylated CREB/ATF1 proteins at 30 min following exposure to isoproterenol (10 µM). As depicted in FIG. 14B, in the absence of isoproterenol, basal levels of phosphorylated CREB/ATF1 protein expression were little affected by transfection with either the scrambled RNA (scRNA; lane 3) or PKA siRNA (lane 5) preparations. By comparison, isoproterenol-induced upregulated expression of phosphorylated CREB/ATF1 (lane 2) was distinctly inhibited in cells transfected with siRNAs directed against PKA (lane 6), whereas the scrambled siRNA sequence had no effect (lane 4). Thus, in concert with the above observations implicating PKA activation in mediating upregulated PDE4 activity in isoproterenol-exposed ASM cells, these data demonstrate that PKA activation is intimately involved in regulating isoproterenol-induced CREB/ATF1 phosphorylation associated with upregulated PDE4D5 expression.

Figure 15:
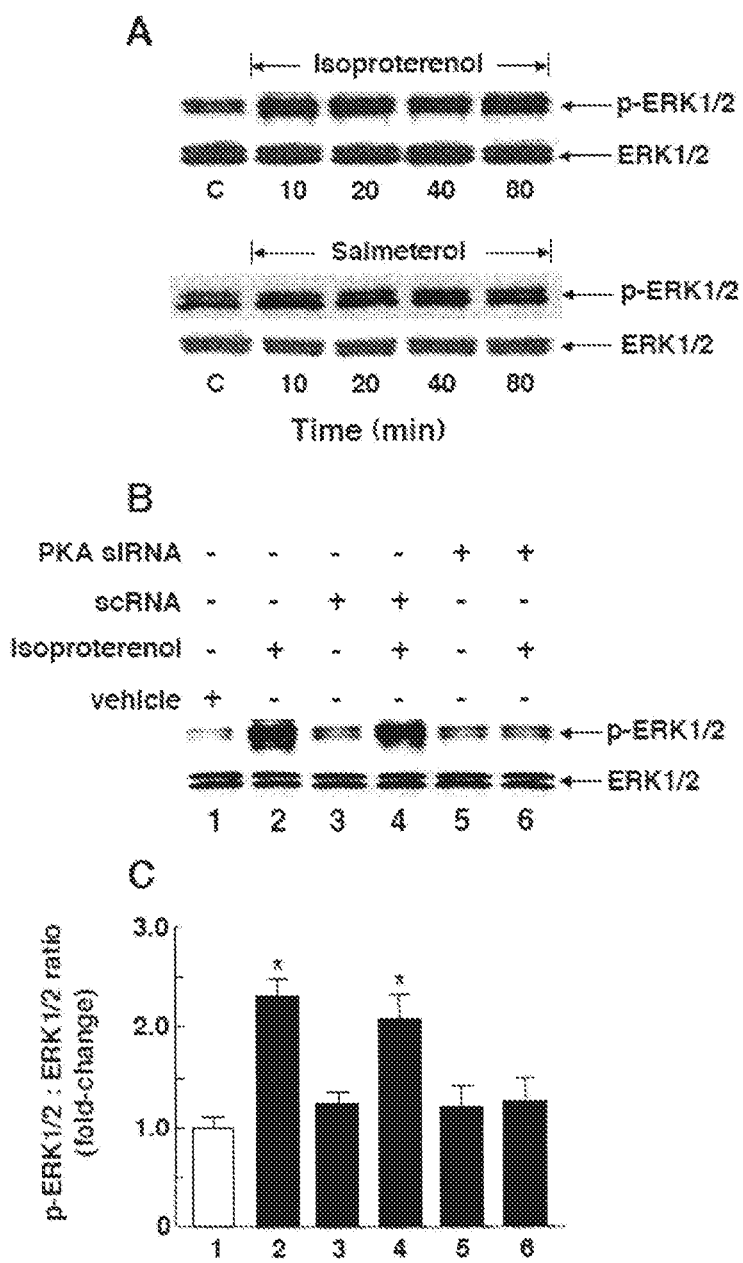
FIG. 15. β2AR stimulation elicits PKA-dependent activation of ERK1/2 in ASM cells. (A) Western blot depicting that isoproterenol or salmeterol acutely evoke enhanced ERK1/2 phosphorylation. (B) Isoproterenol-induced phosphorylation of ERK1/2 is prevented in ASM cells that are transfected with the PKA siRNA duplexes, whereas transfection with a scrambled (control) siRNA duplex (scRNA) has no effect. (C) Corresponding densitometric analysis of the changes in ERK1/2 phosphorylation demonstrates that, relative to control cells (lane 1), β2AR-stimulated cells exhibit a mean 2.3-fold increase in ERK1/2 phosphorylation (lane 2). The latter β2AR agonist-induced phosphorylation of ERK1/2 is prevented in cells pretreated with the PKA siRNA duplexes (lane 6), whereas pretreatment with the scRNA duplex has no effect (lane 4). Data represent mean±SE values based on 3 measurements obtained under each treatment condition. *$p<0.05$.

Apart from the cAMP/PKA pathway, CREB can also be activated via other signaling events, notably including ERK1/2 activation (23). Moreover, in this context, cross-talk between the cAMP/PKA and ERK1/2 signaling pathways has also been demonstrated wherein PKA can activate the Ras/c-Raf1/MEK1/2 and/or the Rap1/B-Raf/MEK1/2 signaling pathway, leading to downstream activation of ERK1/2 (25, 29) which, in turn, can mediate CREB phosphorylation via activation of the CREB kinases, p90RSK or MSK-1 (23). See Example I. Given this evidence, together with the above observations implicating a critical role for ERK1/2 activation in mediating the induced changes in PDE4 expression and in ASM constrictor and relaxation responsiveness in the homologous β2AR-desensitized state, next it was investigated whether β2AR agonist exposure elicits a regulatory interplay between PKA and ERK1/2 signaling in ASM cells. As depicted by representative immunoblots in FIG. 15A, treatment of ASM cells with 10 µM of either isoproterenol or salmeterol acutely elicited increased phosphorylation via ERK1/2 proteins that peaked at 20 min and was sustained for at least up to 80 min. To subsequently assess the role of PKA in mediating this β2AR agonist-induced activation of ERK1/2, ASM cells were first treated for 72 hr with vehicle alone or with either scrambled RNA or siRNAs directed against the PKA catalytic subunits, PKAα and PKAβ, and then examined for induced phosphorylation of ERK1/2 at 20 min following exposure to isoproterenol. As shown in FIG. 15B, relative to vehicle-treated control cells (lane 1), ERK1/2 phosphorylation was markedly increased in isoproterenol-treated cells (lane 2) and, while cells pretreated with either the scrambled or PKA siRNAs preparations alone showed little change in basal ERK1/2 phosphorylation (lanes 3 and 5, respectively), the isoproterenol-induced increase in ERK1/2 phosphorylation was distinctly inhibited in ASM cells that were pretreated with the PKA siRNAs (lane 6), whereas pretreatment of isoproterenol-exposed cells with the scrambled RNA had no appreciable effect (lane 4). Analysis of the results obtained in 4 experiments is depicted in FIG. 15C, wherein the levels of ERK1/2 phosphorylation detected under the different experimental conditions are displayed as mean±SE values of the fold-changes in the densitometric ratios of phosphorylated ERK1/2-to-total ERK1/2. It can be seen that the isoproterenol-induced phosphorylation of ERK1/2 amounted to 2.30±0.18-fold above that detected in control (vehicle-treated) cells (p<0.01) and, in contrast to the lack of effect of scRNA, the β2AR agonist-induced phosphorylation of ERK1/2 was inhibited in cells transfected with PKA siRNA. Thus, these data demonstrate that the induction of ERK1/2 activation in β2AR agonist-exposed ASM cells is regulated by PKA.

Gi-βγ Protein Signaling Mediates PKA-Dependent Activation of ERK1/2 in β2AR Agonist-Exposed ASM.

Figure 16:
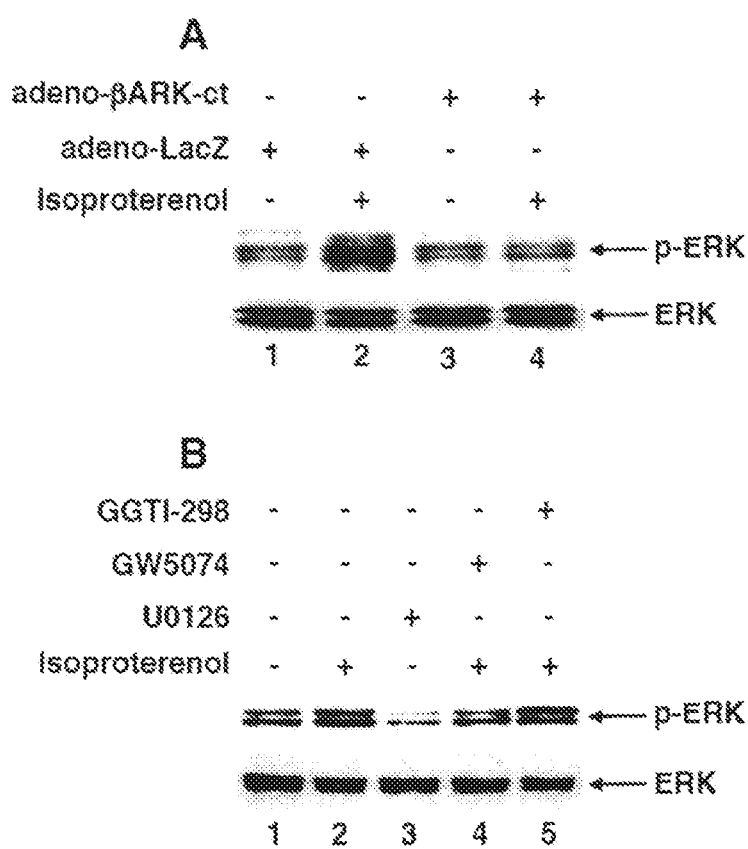
FIG. 16. β2AR agonist-induced phosphorylation of ERK1/2 in ASM cells is mediated by G protein βγ-subunit-mediated activation of the Ras signaling cascade. (A) Western blot showing that, in contrast to ASM cells transfected with adeno-LacZ (i.e., negative control), β2AR agonist-induced ERK1/2 phosphorylation is prevented in ASM cells wherein Gβγ signaling is inhibited by transfection with adeno-βARK-ct. (B) Western blot depicting that pretreatment with the c-Raf1 inhibitor, GW5074, prevents isoproterenol-induced phosphorylation of ERK1/2 in ASM cells, whereas inhibition of Rap1 with GGTI-298 has no effect.

The above observations in β2AR agonist-exposed ASM are consistent with those in Example I wherein it was found that PKA-dependent ERK1/2 activation mediates heterologous β2AR desensitization in ASM evoked by its prolonged exposure to PGE2 or to non-receptor-coupled stimulation of cAMP production with forskolin. The findings in the latter study further demonstrated that PICA-dependent activation of ERK1/2 in PGE2-exposed ASM cells was attributed to Gi-βγ-subunit-mediated activation of Src signaling via the Ras/c-Raf1/MEK1/2 pathway. Given this recent evidence, together with the observations herein that Src and Gi protein activation are intimately involved in mediating β2AR agonist-induced PDE4D5 expression (FIG. 13C), investigation as to whether Gβγ signaling also mediates ERK1/2 activation in 32AR agonist-exposed ASM cells was conducted. This issue was directly addressed in experiments that compared the effects of isoproterenol administration (10 µM×20 min) on ERK1/2 activation in ASM cells at 24 hr following their transfection either with an adenovirus vector expressing lacZ (adeno-LacZ), serving as a negative control, or with adeno-βARK-ct, which encodes the βARK1 carboxyl-terminal domain that blocks Gβγ signaling (25,26), both at a multiplicity of infection (MOI) of 100. As shown in FIG. 16A, cells transfected with adeno-LacZ exhibited distinct isoproterenol-induced ERK1/2 phosphorylation (lane 2), whereas this response to isoproterenol was completely ablated in cells transfected with adeno-βARK-ct (lane 4), implicating Gβγ signaling in mediating ERK1/2 activation by the β2AR agonist. In light of these data, together with earlier reports demonstrating that PKA-dependent activation of ERK1/2 can occur via Gi-βγ subunit-mediated stimulation of Src-induced signaling via either the Rap1/B-Raf/MEK1/2 or the Ras/c-Raf1/MEK1/2 pathway (27), examination was undertaken to determine whether the observed Gβγ-mediated activation of ERK1/2 in β2AR agonist-exposed ASM is attributed to induced downstream signaling via the Rap1/B-Raf/MEK1/2 and/or the Ras/c-Raf1/MEK1/2 pathway. Accordingly, to ascertain the relative contributions of these downstream signaling pathways, the effects of selective inhibitors of c-Raf1 and Rap1 activation on β2AR agonist-induced ERK1/2 phosphorylation was compared. As depicted in FIG. 16B, relative to control (vehicle-exposed) cells (lane 1), ASM cells exposed to isoproterenol (10 μM×20 min) exhibited increased expression of phosphorylated ERK1/2 (lane 2) and, as expected, activation of ERK1/2 was ablated by pretreating the cells with the selective MEK-ERK1/2 inhibitor, U0126 (lane 3). By comparison, pretreatment with the selective c-Raf1 inhibitor, GW5074 (20 μM), completely abrogated the stimulatory effect of isoproterenol on ERK1/2 phosphorylation (lane 4), whereas cells pretreated with GGTI-298 (25 μM), a potent selective inhibitor of Rap1 activation (27), did not exhibit attenuated isoproterenol-induced ERK1/2 phosphorylation (lane 5). Thus, together with the above results, these observations support the concept that activation of ERK1/2 in β2AR agonist-exposed ASM cells is attributed to PKA-dependent activation of Gi-βγ-mediated signaling, the latter leading to Src-induced stimulation of the Ras/c-Raf1/MEK-ERK1/2 pathway.

EXAMPLE III

Agents which Inhibit Gβγ Protein Signaling and Methods of Use Thereof for the Treatment Asthma As described above in Example I, the mechanism underlying pro-asthmatic changes in airway smooth muscle (ASM) constrictor and relaxation responsiveness accompanying heterologous β2AR desensitization induced by prolonged exposure of the ASM to either the receptor- or non-receptor-mediated cAMP-elevating agent, PGE$_2$, β2-adrenergic agents, or forskolin, respectively has been elucidated. Rabbit ASM tissues and human ASM cells treated for 24 hours with either of these cAMP-stimulating agents exhibited constrictor hyperresponsiveness to acetylcholine and impaired β2AR-mediated relaxation and cAMP accumulation. These pro-asthmatic-like changes in ASM function were mediated by upregulated PDE4 activity, associated with increased transcription of the PDE4D5 isoform, and this phenomenon was attributed to activation of the ERK1/2 module by protein kinase A (PKA)-dependent activation of G$_i$ protein signaling via the βγ-subunit. Given this evidence, it was hypothesized that signaling via the Gi-βγ-subunit in ASM mediates pro-asthmatic changes in ASM function. This hypothesis was tested by treating rabbit ASM tissues and human ASM cells with cell membrane-permeable peptides that disrupt specific protein-protein interactions by mimicking protein-binding domains. The blocking peptides are rendered cell-permeable by incorporating a membrane-permeable sequence (MPS) designed from the signal sequence of Karposi fibroblast growth factor, which was previously shown to translocate covalently attached peptides across the cell membrane (Zhang, L et al. (1996) *Anal. Biochem.* 233: 87-93; Zhang, L., et al. (1998) *Proc. Natl. Acad. Sci. USA*. 95: 9184-9189; Lin, Y. Z., et al. (1995) *J. Biol. Chem.* 270: 14255-14258; Liu, K. Y., et al. (1996) *Proc. Natl. Acad. Sci. USA*. 93: 11819-11824; Rojas, M., et al. (1996) *J. Biol. Chem.* 271: 27456-27461; Chang, M. S. S., Tam et al. (2000) *Science's STKE*, on the World Wide Web at: stke.org/cgi/content/full/OC_sigtrans; 2000/47/p 11). Previous studies have confirmed that functional peptides attached to the MPS sequence are membrane penetrating and lack short-term cell toxicity (Zhang, L., et al. (1998) *Proc. Natl. Acad. Sci. USA*. 95: 9184-9189; Lin, Y. Z., et al. (1995) *J. Biol. Chem.* 270: 14255-14258).

The results reveal that a MPS-attached blocking peptide directed against free Gβγ subunits inhibits the induction of pro-asthmatic changes in constrictor and relaxation responsiveness in ASM subjected to heterologous β2AR desensitization by prolonged exposure of the ASM to PGE$_2$, as well as in ASM passively sensitized with serum isolated from allergic asthmatic rabbits.

Methods:

The animal preparation and pharmacodynamic methods used in this study are as described in Example I. To test the effects of blockade of specific G protein subunits, a MPS-attached blocking peptide directed against free Gβγ subunits was used, as well as MPS-attached blocking peptides directed against the Gαi2 and Gαi3 units. The MPS-attached peptides were purchased from AnaSpec, and consisted of the following sequences:

```
Anti-Gβγ (MPS-Phosducin-like protein C terminus):
                                         (SEQ ID NO: 1)
1-letter code:
AAVALLPAVLLALLAVTDQLGEDFFAVDLEAFLQEFGLLPEKE MPS- Gαi3:
                                         (SEQ ID NO: 6)
1-letter code:
AAVALLPAVLLALLAKNNLKECGLY MPS- Gαi2:
                                         (SEQ ID NO: 7)
1-letter code:
AAVALLPAVLLALLAKNNLKDCGLF
```

Results:
Effect of MPS-Anti-Gβγ Peptide on ASM Responsiveness in PGE$_2$-Exposed Rabbit ASM Tissues.

Figure 17:
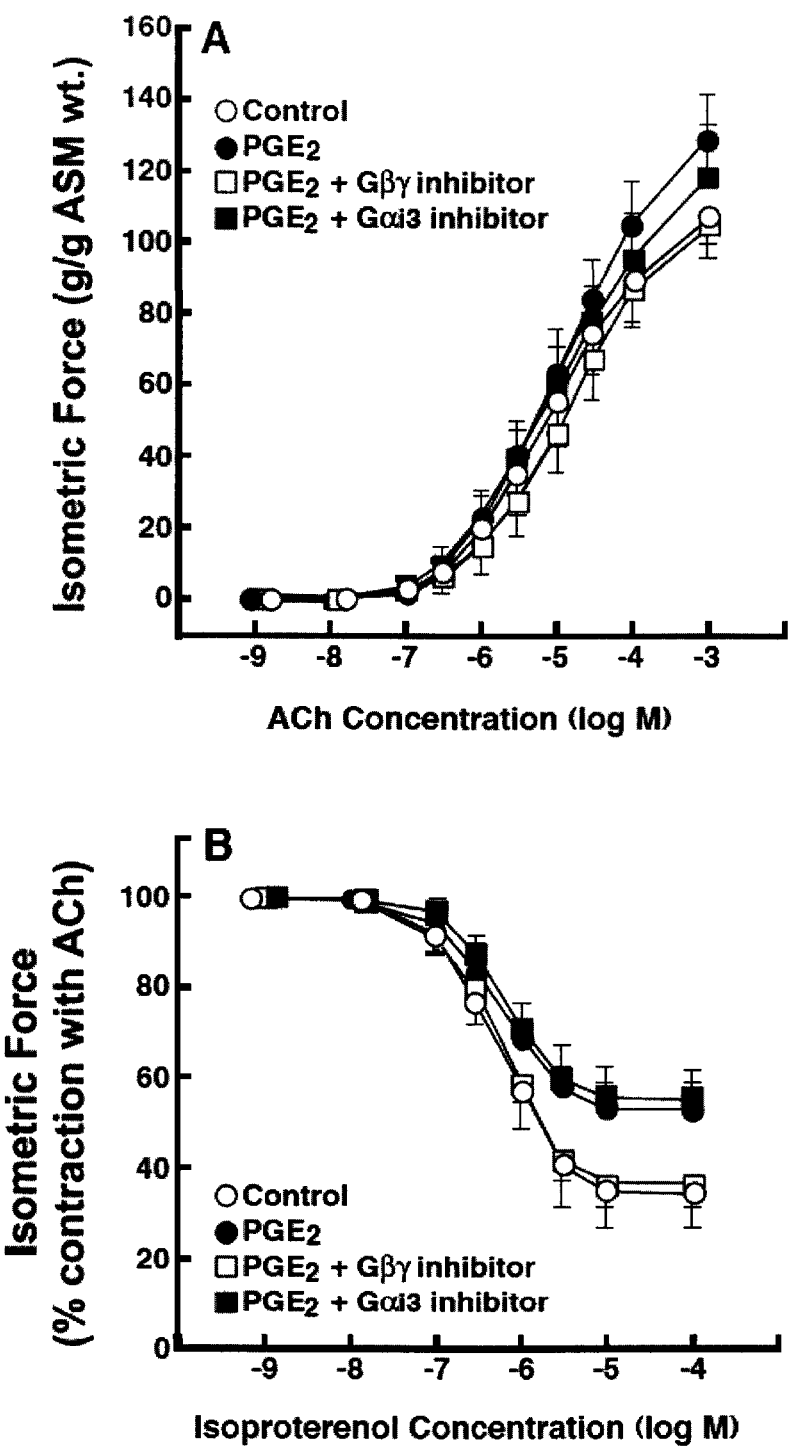
FIG. 17. Pretreatment with the Gβγ inhibitory peptide prevents the induction of altered ASM tissue constrictor and relaxation responsiveness accompanying heterologous β2AR desensitization. Relative to vehicle-treated controls, rabbit ASM tissues exposed for 24 hr to PGE2 (100 nM) exhibit significantly increased constrictor responses to ACh (A) and impaired relaxation responses to isoproterenol (B). Pretreatment with the Gβγ inhibitory peptide (30 μM), prevents these PGE2-induced changes in ASM constrictor and relaxation responsiveness. By comparison, pretreatment with an Gαi3 inhibitory peptide has no effect on PGE2-induced changes in ASM responsiveness. Data represent mean±SE values from 4 paired experiments.

In accordance with the previous observations (see Example I), rabbit ASM tissues exposed for 24 hours to PGE$_2$ (100 nM) exhibited increased constrictor responsiveness to ACh (FIG. 17A) and impaired ASM relaxation to isoproterenol (FIG. 17B). These pro-asthmatic-like changes in ASM responsiveness were prevented by pre-treating the PGE$_2$-exposed ASM tissues with the anti-Gβγ cell-permeable inhibitory peptide (30 μM), whereas pre-treating the tissues with the anti-Gαi3 blocking peptide had no effect.

Effect of MPS-Anti-Gβγ Peptide on cAMP PDE Activity in PGE$_2$-Exposed Human ASM Cells.

Figure 18:
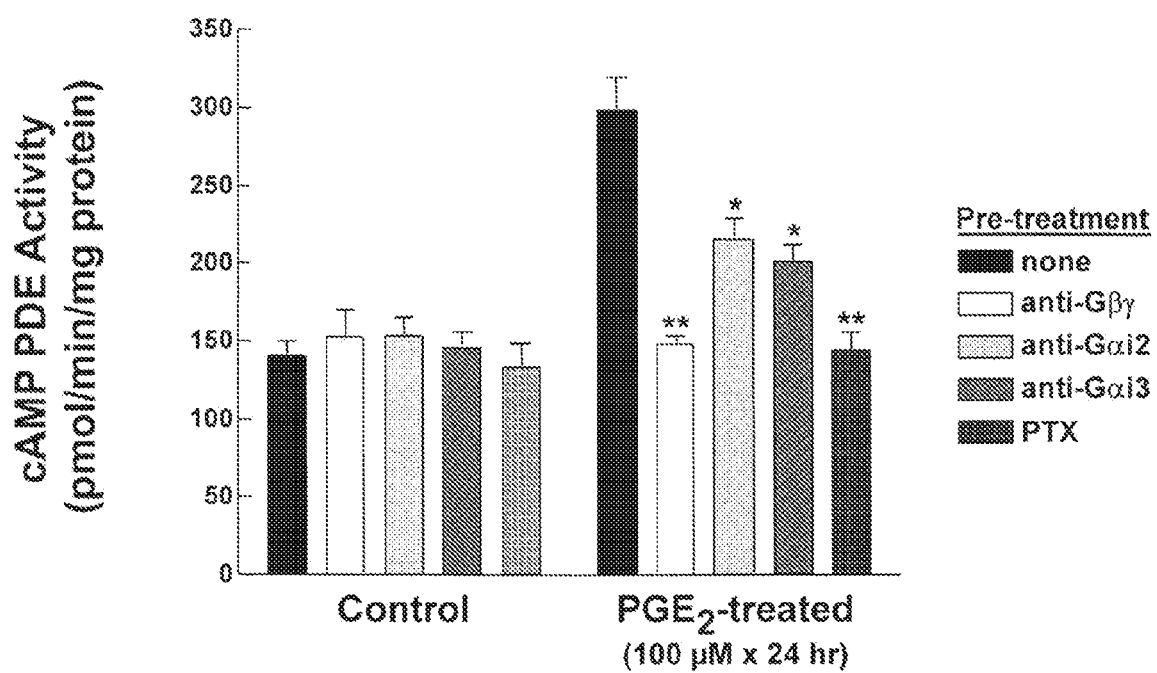
FIG. 18. Pretreatment with the anti-Gβγ inhibitory peptide prevents the induction of cAMP PDE4 activity in cultured human ASM cells exposed to PGE2. Relative to vehicle-treated (control) ASM cells, levels of PDE4 activity are significantly increased in cells exposed for 24 hr to 100 nM of PGE2. The stimulated PDE activity is completely ablated in PGE2-exposed ASM cells that are pretreated either with the Gβγ inhibitory peptide or with PTX, whereas pretreatment with the anti-Gαi2 or anti-Gαi3 inhibitory peptide only exerts a partial inhibitory effect. Data represent mean±SE values from 3 measurements made under each treatment condition. *$p<0.05$; **$p<0.01$.

As described above in Example I, the induction of pro-asthmatic changes in constrictor and relaxation responsiveness in ASM exposed for 24 hours to PGE$_2$ is attributed to an induced increase in PDE4 activity. This phenomenon is depicted in FIG. 18 wherein, relative to control (vehicle-exposed) cells, ASM cells exposed for 24 hours to PGE$_2$ (100 nM) exhibit a significant increase in PDE activity. It will be noted that the stimulatory effect of $PGE_2$ on PDE activity is completely abrogated by pretreating the $PGE_2$-exposed ASM cells with the anti-Gβγ cell-permeable inhibitory peptide (30 μM), whereas pre-treating the cells with either the Gαi2 or Gαi3 blocking peptide had only a partial inhibitory effect. In this regard, it is further noteworthy that the complete inhibitory effect of the anti-Gβγ peptide on $PGE_2$-induced PDE activity is similar to that obtained when pretreating the $PGE_2$-exposed ASM cells with pertussis toxin (PTX), as described above.

Effect of MPS-Anti-Gβγ Peptide on ASM Responsiveness in Asthmatic Serum-Sensitized Rabbit ASM Tissues.

Figure 19:
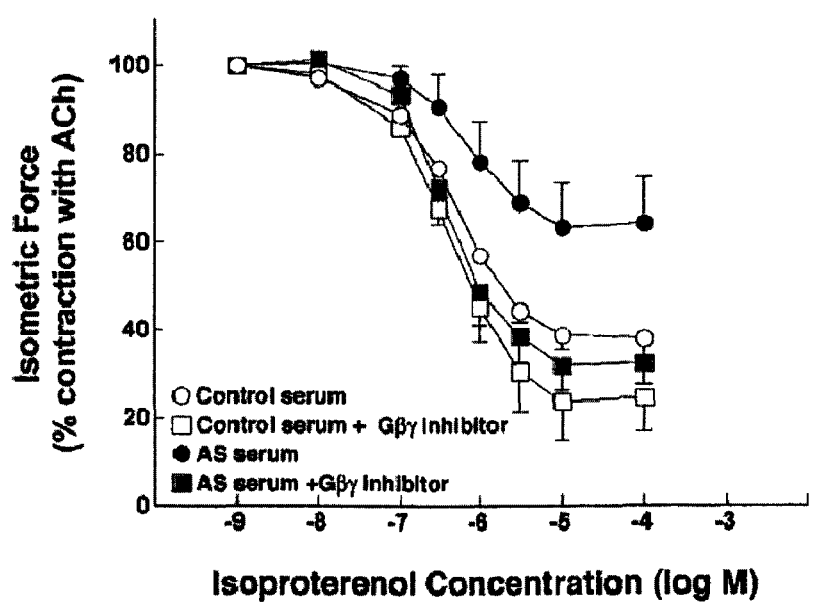
FIG. 19. Pretreatment with the Gβγ inhibitory peptide prevents the induction of altered relaxation responsiveness in ASM tissues passively sensitized with allergic asthmatic (AS) serum. Relative to tissues exposed to control (non-asthmatic) serum, rabbit ASM tissues exposed for 24 hr to AS serum exhibit significantly impaired relaxation responses to isoproterenol. The induction of impaired relaxation is prevented in AS serum-exposed ASM tissues by pretreating the tissues with the Gβγ inhibitory peptide, and the latter also enhances the relaxation responses to isoproterenol in control serum-exposed tissues. Data represent mean±SE values from 3 paired experiments.

In light of the above evidence that the Gβγ-inhibitory peptide effectively prevents the induction of pro-asthmatic changes in ASM responsiveness in $PGE_2$-exposed cells, examination was conducted to determine whether pretreatment with the Gβγ-inhibitory peptide also has a protective effect in preventing the induction of altered ASM responsiveness in rabbit ASM tissues passively sensitized for 24 hours with serum from allergic asthmatic rabbits (e.g., rendered asthmatic by immunizing rabbits with weekly (4-6 weeks) intraperitoneal injections of an allergen (ovalbumin) in adjuvant, and thereafter challenging animals with inhalation of the immunogen). As shown in FIG. 19, relative to ASM tissues exposed to serum isolated from non-asthmatic (control) rabbits, ASM tissues exposed to allergic asthmatic (AS) serum exhibit markedly decreased relaxation responsiveness to isoproterenol. This impaired relaxation to isoproterenol is prevented by pretreating the AS serum-exposed ASM tissues with the Gβγ-inhibitory peptide. Interestingly, the relaxation responses to isoproterenol are also somewhat increased in control serum-exposed ASM tissues that are pretreated with the Gβγ-inhibitory peptide.

$G_i$-βγ Signaling Regulates PDE4 Activity and Constrictor and Relaxation Responsiveness in Homologous β2AR-Desensitized ASM.

Figure 20:
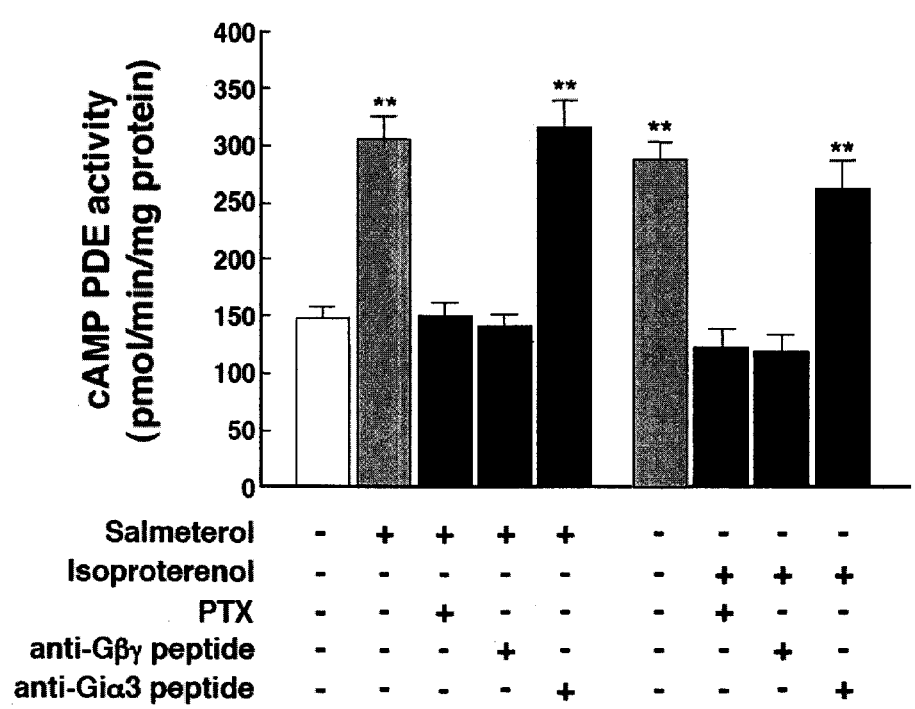
FIG. 20. Gi-βγ signaling mediates upregulated PDE activity in prolonged β2AR-stimulated ASM cells. PDE4 activity is significantly increased in ASM cells exposed for 24 hr to 10 μM of isoproterenol or salmeterol. Stimulation of cAMP PDE activity is ablated in β2AR-exposed ASM cells by ADP ribosylation of Gi protein with PTX or by blockage of the βγ subunits of G protein with anti-Gβγ peptide conjugated to a membrane permeable peptide sequence (MPS), whereas pretreatment with the MPS-conjugated anti-$G_i$β3 peptide has no effect. Data represent mean±SE values based on 4 measurements obtained under each treatment condition. **$p<0.01$.
Figure 21:
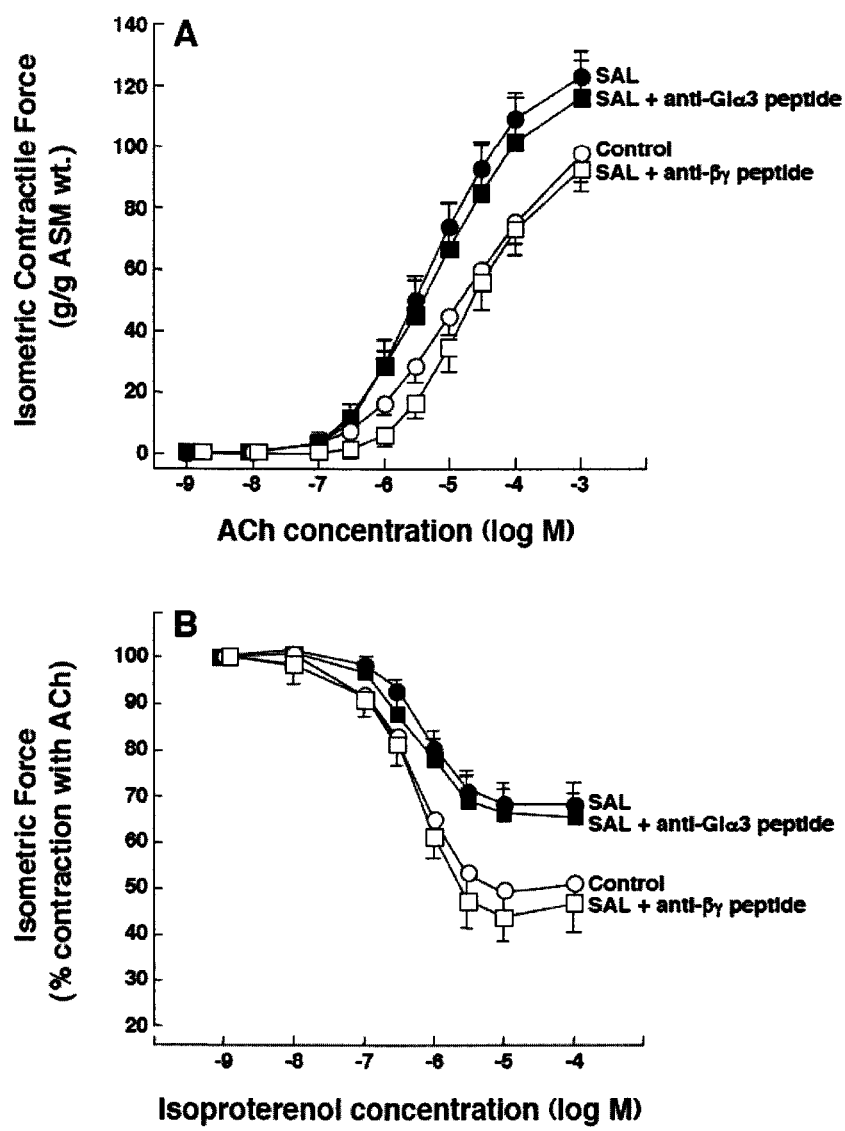
FIG. 21. Changes in ASM constrictor and relaxation responsiveness accompanying salmeterol-induced homologous β2AR desensitization are mediated by Gβγ signaling. Relative to vehicle-treated controls, rabbit ASM tissues exposed for 24 hr to salmeterol exhibit significantly increased constrictor responses to ACh (A) and impaired relaxation responses to isoproterenol (B). The salmeterol-induced changes in ASM constrictor and relaxation responsiveness are ablated in tissues that are pre-treated with the MPS-conjugated anti-Gβγ peptide, whereas pretreatment with the MPS-conjugated anti-$G_i$α3 peptide has no effect. Data represent mean±SE values from 4 paired experiments.

To ascertain the physiological implications of the above mechanism of $G_i$-βγ-mediated interplay between the PKA and ERK1/2 signaling pathways in the homologous β2AR-desensitized state, the effects of inhibition of $G_i$ protein function and Gβγ-specific signaling on the changes in PDE activity and constrictor and relaxation responsiveness induced by prolonged homologous β2AR desensitization in human ASM cells and rabbit tissues, respectively, was examined. As shown in FIG. 20, relative to untreated (vehicle-exposed) control ASM cells, cAMP PDE activity was significantly increased in cells that were incubated for 24 hr with 10 μM of salmeterol or isoproterenol, and this stimulation of PDE4 by either β2AR agonist was completely abrogated in cells wherein $G_i$ protein signaling was interrupted by pretreatment with PTX (100 ng/ml) or with 1 μM of a Gβγ-specific sequestering peptide (anti-Gβγ peptide) coupled to a cell membrane permeable carrier peptide sequence (MPS). By comparison, stimulation of PDE activity by either β2AR agonist was unaffected in cells pretreated with a MPS-coupled peptide directed at inhibiting $G_i$α3 signaling (anti-$G_i$α3 peptide; 1 μM). Comparably, as depicted in FIG. 21, relative to the responses obtained in control rabbit ASM tissues, the significantly increased constrictor responses to ACh (FIG. 21A) and impaired relaxation responses to isoproterenol (FIG. 21B) detected in salmeterol-exposed ASM tissues were prevented by pretreating these tissues with the anti-Gβγ peptide (30 μM), whereas pretreatment with the anti-$G_i$α3 peptide (30 μM) had no effect. In relation to these observations, it should be noted that in separate studies wherein vehicle-exposed control ASM tissues were comparably pretreated with the latter inhibitory peptides, there was no significant effect of either peptide on the tissues' constrictor or relaxation responses (data not shown). Thus, these data provide physiological evidence supporting the notion that the above $G_i$-βγ-coupled mechanism of β2AR agonist-induced cross-talk between the cAMP/PKA and ERK1/2 signaling pathways mediates the rolipram-sensitive changes in PDE activity and ASM constrictor and relaxation responsiveness (FIGS. 11 and 12, respectively) that are exhibited in the homologous β2AR-desensitized state.

Figure 22:
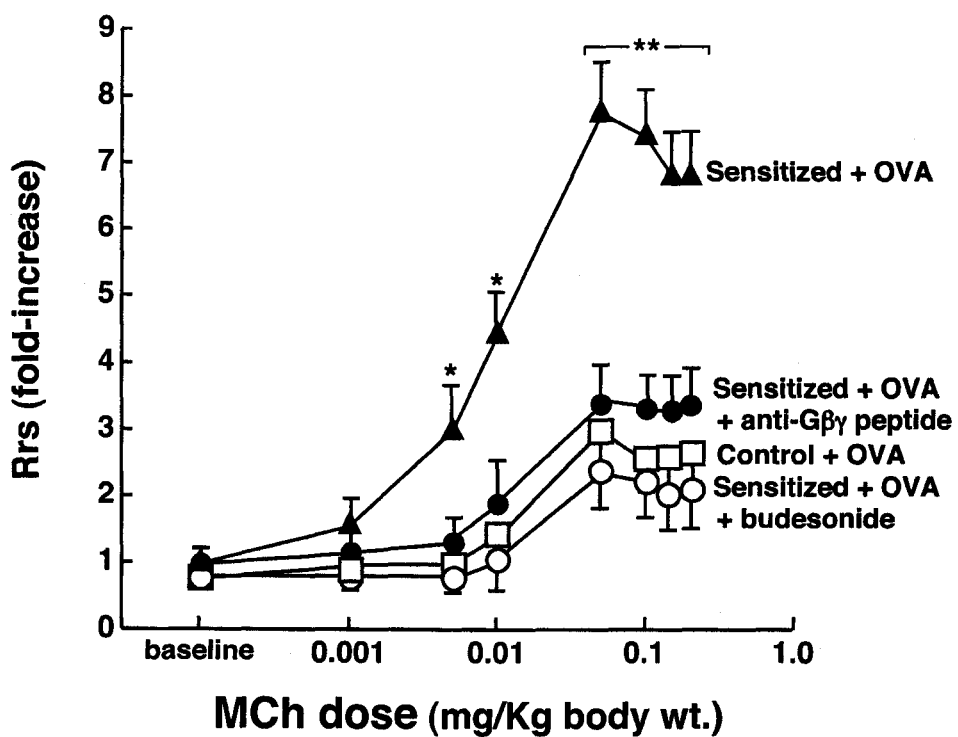
FIG. 22. Comparison of in vivo bronchoconstrictor responses to MCh in non-sensitized (control) and OVA-sensitized rabbits challenged with OVA in the absence and presence of pretreatment with either budesonide or anti-G βγ peptide. Note: relative to control (non-sensitized) rabbits, airway responsiveness to MCh, assessed as induced fold-increases above control (baseline) in respiratory system resistance (Rrs), is markedly increased in OVA-sensitized+OVA challenged rabbits, and this heightened bronchoconstrictor responsiveness is prevented to a similar degree by pretreating the sensitized rabbits with either budesonide or the MPS-conjugated anti-G βγ peptide. Data are mean±SE values. *p<0.05; **p<0.01.
Figure 23:
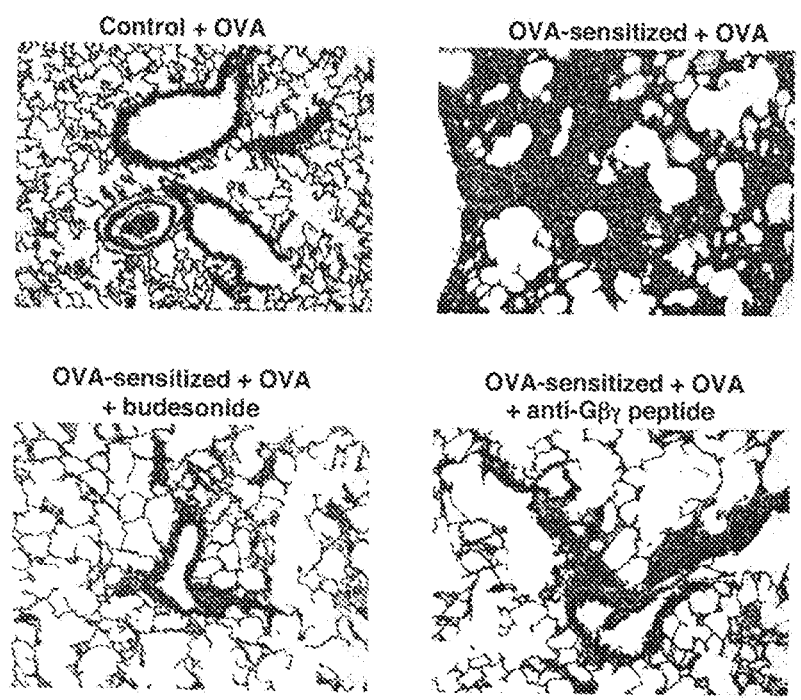
FIG. 23. Photomicrographs comparing lung histopathology in 4 μm sections of lung tissues isolated from representative control (non-sensitized) rabbits and OVA-sensitized rabbits challenged with OVA in the absence and presence of pretreatment with either budesonide or anti-Gβγ peptide. Note: pretreatment with either the anti-Gβγ peptide or budesonide markedly suppresses to a similar extent the pulmonary inflammatory response in OVA-sensitized+OVA challenged rabbits.
Figure 24:
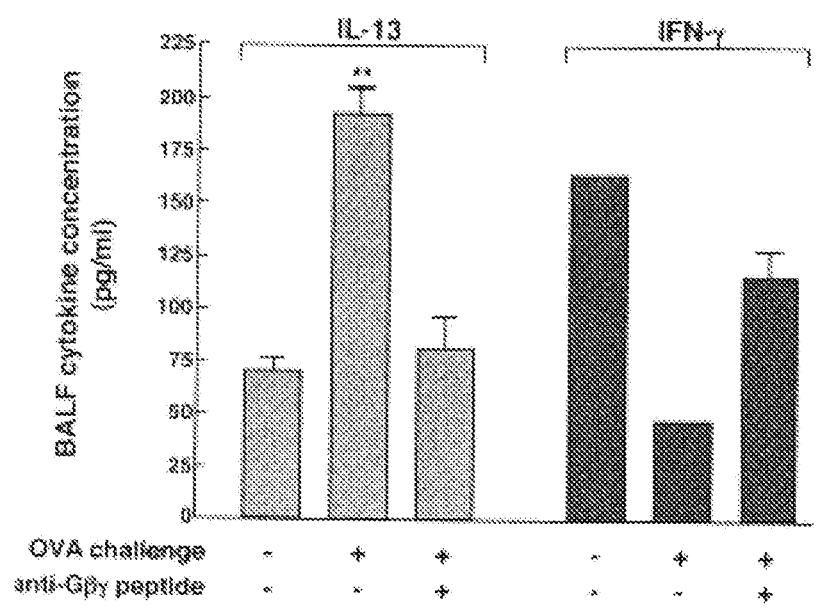
FIG. 24. Comparison of concentrations of IL-13 and IFN-γ in BALF samples isolated from sensitized rabbits in the absence and presence of OVA challenge, with and without pretreatment of the rabbits with the anti-Gβγ peptide. Note: pretreatment with the anti-Gβγ peptide prevents the increase in IL-13 and decrease in IFN-γ cytokine levels that are elicited by OVA challenge in sensitized rabbits.

In vivo studies were conducted wherein adult NZW rabbits were initially sensitized with weekly intra-peritoneal (i.p.) injections of 2.5 mg OVA and 10 mg of alum adjuvant for 4-5 weeks, and non-sensitized (control) rabbits received alum alone. Both the OVA sensitized and control animals were then challenged with either vehicle (saline) or aerosolized OVA delivered via a nebulizer. The following day, while mechanically ventilated under general anesthesia/paralysis, the rabbits' broncho-constrictor responses to intravenous (i.v.) bolus injections of cumulatively increasing doses of methacholine (MCh) were determined and induced changes in respiratory system resistance (Rrs), measured as previously described (Grunstein et al. J. Appl. Physiol: Respirat. Environ. Exercise Physiol. 57:1238-1246, 1984). Lung lavage was then performed to obtain bronchoalveolar lavage fluid (BALF) samples, and the lungs were excised for histological examination in H&E-stained paraffin-embedded 4 micron sections. FIG. 22 demonstrates that, relative to control (non-sensitized) rabbits exposed to OVA, the Rrs responses to MCh are significantly increased in the sensitized rabbits at 24 hr following inhaled OVA-challenge; and this airway constrictor hyper-responsiveness is largely abrogated in sensitized+OVA-exposed rabbits that are pretreated at 2 hr prior to OVA challenge with either: 1) the anti-Gβγ peptide, delivered at a maximally effective dose of 1 mg/Kg by inhalation via a nebulizer connected to a mask placed over the nose and mouth; or 2) budesonide (1 mg/Kg), an inhaled corticosteroid commonly used to treat asthma, also administered by airway nebulization. Comparably, the photomicrographs in FIG. 23 demonstrate that, relative to control+OVA exposed lungs that show normal parenchyma and airways with no sign of inflammation: 1) the OVA-sensitized+OVA challenged lungs exhibit dense peribronchial and parenchymal inflammatory cell infiltration; and 2) this inflammatory response is markedly suppressed to a similar extent in the lungs of OVA-sensitized+OVA challenged rabbits that are pretreated with either budesonide or the anti-Gβγ peptide. Consistent with these findings, as shown in FIG. 24, BALF analysis demonstrates a striking increase in the concentration of the pro-asthmatic Th2-type cytokine, IL-13, and decrease in the Th1-type cytokine, IFN-γ, in the BALF samples from the OVA-sensitized+OVA challenged rabbits, and that both these changes in cytokine release are prevented in rabbits pretreated with the anti-Gβγ peptide. Taken together, these data demonstrate that inhalation of the anti-Gβγ peptide is highly efficacious in preventing both the in vivo pulmonary inflammation and airway hyperresponsiveness that is elicited by allergen challenge in allergic asthmatic rabbits.

Discussion

Despite the fact that inhaled β2AR agonists are a very effective approach to acutely relieve the airway broncho-spasm resulting from the altered ASM constrictor and relaxation responsiveness characteristic of asthma, there is compelling evidence demonstrating that prolonged β2AR stimulation following chronic use of long acting β2AR agonists is associated with worsening of the asthmatic condition and subsequent increase in morbidity and mortality (4, 31, 37). These pro-asthmatic-like changes are believed to result from homologous desensitization of the airways to the bronchodilatory action of β2AR agonists. Previous studies have attributed the generation of β2AR desensitization to the phosphorylation of the β2AR and, hence, its uncoupling from Gs protein-mediated cAMP production (12, 15, 35, 39). Accordingly, the role played by phosphorylation of the β2AR by G protein-coupled receptor (GPCR) kinases (GRKs) and cAMP-dependent protein kinase A (PKA) in mediating homologous β2AR desensitization has been demonstrated acutely following exposure of ASM cells to β2AR agonists. This acute loss of β2AR function contrasts with the clinical worsening of asthma that needs prolonged use of β2AR agonists to occur (Cheung (1992) N Engl. J. Med. 327:1198-1203; Wong et al. (1997) Eur. Resp. J. 10:330-336; Yates et al. (1997) 156:988-91). In fact, prolonged β2AR stimulation of ASM seems to be necessary for an intracellular mechanism to underlie the worsening of asthma induced by β2AR agonists. This is illustrated by the clinical observation that acute β2AR agonist administration transiently improves the bronchoconstriction seen in asthma whereas the chronic use of long acting β2AR agonists leads to loss of this bronchoprotective effect and to enhanced bronchoconstrictor responsiveness to cholinergic stimulation (12). As shown in Example I, the pro-asthmatic-like changes in ASM constrictor and relaxation responsiveness evoked by prolonged heterologous β2AR desensitization are attributed to an induced increase in PDE4 activity mediated by a cAMP/PKA dependent Gi-βγ signaling which, in turn, elicits downstream MEK/ERK1/2 activation. In addition, PDE4 activity has been previously reported to play a fundamental role in regulating the altered ASM contractility and in mediating the constrictor hyper-responsiveness of the airways seen in allergic asthma (8, 21, 24, 41, 43). Other studies have documented that the impaired relaxant responsiveness to β2AR stimulation in ASM exposed to various pro-asthmatic conditions is also attributed to upregulated expression and action of Gi protein, which attenuates cAMP accumulation and, hence, the bronchodilatory action of β2AR agonists (17, 18, 19, 34). Moreover, recent reports have implicated a critical role for ERK1/2 signaling in mediating both the impaired β2AR-mediated relaxation and increased constrictor responsiveness in ASM exposed to different pro-asthmatic stimuli (14, 28, 38). Here, new evidence is provided demonstrating that: 1) the pro-asthmatic-like changes in ASM constrictor and relaxation responsiveness accompanying homologous β2AR desensitization resulting from prolonged exposure to β2AR agonists are mediated by upregulated PDE4 activity; 2) the latter is attributed to PKA-dependent induction of Gi-βγ-generated signaling that involves Src-mediated downstream activation of ERK1/2 which, in turn, leads to transcriptional upregulation of PDE4 expression and its consequent action. These novel findings highlight a mechanism that potentially elucidates the well-established association between prolonged airway desensitization to β2AR agonists and aggravation of the asthmatic phenotype.

The physiologic relevance of the above interplay between PKA activation and Gi-βγ-mediated ERK1/2 signaling in regulating the rolipram-sensitive changes in ASM function associated with homologous β2AR desensitization was supported by the observations that the upregulated cAMP PDE activity in human ASM cells following prolonged β2AR stimulation by either salmeterol or isoproterenol, was prevented by either ADP ribosylation of Gi protein using PTX or by specific blockage of the βγ subunit of Gi using the membrane permeable anti-βγ peptide, MPS-phosducin-like protein (FIG. 20). By comparison, stimulation of cAMP PDE activity by either β2AR agonist was unaffected in cells pretreated with a MPS-coupled peptide directed at inhibiting Giα3 signaling (FIG. 20). Moreover, the pro-asthmatic-like changes in contraction and relaxation induced by prolonged β2AR stimulation in the ASM tissues were ablated by pretreatment with the membrane permeable anti-βγ peptide, MPS-phosducin-like protein, whereas pretreating the salmeterol-exposed tissues with the anti-Giα3 peptide had no effect (FIG. 21). These findings are in general agreement with the previous study that reported key regulatory roles for PKA, ERK1/2 and Gi-βγ signaling in mediating heterologous β2AR desensitization and overall demonstrate that the above mechanisms of PDE4 upregulation play a decisive role in mediating the pro-asthmatic-like changes in both ASM constrictor and relaxation responsiveness that accompany prolonged homologous β2AR desensitization. The results obtained also demonstrate in smooth airway tissue samples are recapitulated in vivo. See FIGS. 22-24.

To summarize, the present study examined the regulation and role of PDE4 activity in mediating the changes in ASM constrictor and relaxation responsiveness associated with homologous β2AR desensitization. The results provide new evidence demonstrating that: 1) homologous β2AR desensitization in ASM elicits attenuated cAMP accumulation and increased cholinergic agonist mediated ASM constrictor responsiveness together with impaired β2AR-mediated ASM relaxation; 2) these changes in ASM function are mediated by transcriptional upregulation of PDE4 activity, reflected by increased expression of the PDE4D5 isoform; 3) the upregulated expression of PDE4D5 is attributed to PKA-dependent activation of Gi protein signaling, resulting in Gi-βγ-subunit-mediated downstream activation of ERK1/2 via the Src/Ras/Raf1/MEK1/2 signaling pathway) the latter activation of ERK1/2, in turn, leads to phosphorylation of the transcription factors, CREB and ATF1, which mediate CRE-driven PDE4D5 gene transcription.

Collectively, these new findings identify that the pro-asthmatic-like changes in ASM function that accompany prolonged airway exposure to β2AR agonists are mediated by upregulated PDE4 activity that is attributed to an induced cross-talk between the cAMP/PKA and ERK1/2 signaling pathways. Thus, interventions targeted at regulatory sites within this cross-talk mechanism may provide novel therapeutic approaches to mitigate the aggravated asthmatic condition associated with chronic use of long acting β2AR agonist in asthma. Indeed, the data indicate that administration of a MPS-associated anti-Gβγ peptide represents an effective new therapeutic approach for the treatment of asthma.

EXAMPLE IV

Use of a Membrane Permeable Gβγ Blocking Peptide to Treat Inflamatory Ocular Disorders The previous examples describe use of a membrane-permeable peptide sequence (MPS) attached to a blocking peptide directed against the beta-gamma subunits of Gi protein (MPS:anti-Gβγ peptide) which is effective to inhibit the induction of pro-asthmatic changes in constrictor and relaxation responsiveness in airway smooth muscle (ASM) subjected to beta2-adrenergic receptor (β2AR) desensitization. This composition is also effective in ASM passively sensitized with serum isolated from allergic asthmatic rabbits and, moreover, the composition inhibits the induction of airway hyerresponsiveness and pulmonary inflammation in allergic asthmatic rabbits in vivo In the present example, topical application of the MPS: anti-Gβγ peptide to the surface of the eye is described. The present inventor has discovered that administration of the peptide prevents the allergic conjunctivitis response in vivo that is elicited by exposure of the eye to a sensitizing antigen in an allergic animal model. Notably, the invention avoids the adverse effects associated with chronic use of topical steroids by either eliminating or significantly reducing the need for steroids (as well as other medications) to treat conjunctivitis. The new evidence disclosed herein provides the basis for clinical use of the MPS:anti-Gβγ peptide for the treatment of allergic conjunctivitis. The compositions described should also be effective for treatment of non-allergic conjunctivitis induced by exposure of the eyes to irritant chemicals etc. Moreover, the evidence disclosed indicates that MPS:anti-Gβγ peptide can be used to effectively treat other allergic disorders including allergic rhinitis and atopic dermatitis, and also non-allergic rhinitis and dermatitis induced by irritant chemicals.

Figure 25:
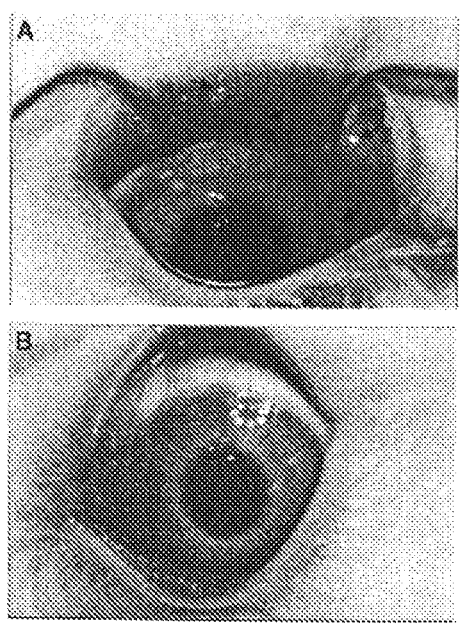
FIG. 25. Comparison of responses to ocular OVA challenge in right (A: "sham" MPS alone pretreated) and left (B: MPS-conjugated anti-Gβγ peptide-pretreated) eyes at 60 minutes following OVA challenge in an OVA-sensitized rabbit. Note: arrows indicate sites of conjunctival injection, vascular engorgement, and chemosis present in the OVA-exposed "sham"-pretreated eye, while signs of allergic conjunctivitis are absent in the MPS-conjugated anti-Gβγ peptide-pretreated eye.

Similar to previous studies investigating either allergic asthma or allergic conjunctivitis in animal models, in vivo studies were conducted wherein adult NZW rabbits were initially systemically immunized with weekly intra-peritoneal (i.p.) injections of 2.5 mg ovalbumin (OVA) and 10 mg of alum adjuvant for 4-5 weeks. Following sensitization, as previously described in other animal models of allergic conjunctivitis (Groneberg D. A. et al. Allergy 58: 1101-1113, 2003), the OVA allergen was topically introduced into the conjunctival sac of the eyes of the rabbit to examine its ocular allergic inflammatory response. Specifically, examination was conducted to determine whether the anti-inflammatory action exhibited by the anti-Gβγ peptide in the treatment of allergic asthma described in Examples I and II is also applicable to treating allergic conjunctivitis which occurs in response to ocular OVA antigen challenge in OVA sensitized rabbits. Accordingly, for each animal, 15 µl of a sterile 1 µM concentration of the MPS:anti-Gβγ peptide (prepared in PBS) was topically applied into the conjunctival sac of one eye 20 minutes prior to subsequent instillation of OVA (500 µg in 15 µl PBS), and the carrier MPS peptide alone (i.e., control "sham" pretreatment) was applied to the other eye 20 minutes prior to subsequent instillation of OVA. The eyes were then clinically examined for an acute ocular inflammatory response to OVA challenge and photographs were taken of each eye at 60 minutes following OVA challenge. As representatively depicted in FIG. 25, the "sham" control eye exposed to OVA demonstrated conjunctival injection, vascular engorgement, and chemosis (hyperemic and edematous conjunctiva), all characteristic features of allergic conjunctivitis. By comparison, the eye pretreated with the anti-Gβγ peptide showed virtually no clinical signs of conjunctival inflammation. These findings provide evidence that topical application of the anti-Gβγ peptide to the surface of the eye is highly efficacious in preventing the allergic conjunctivitis response to allergen exposure in vivo. Additionally, the anti-Gβγ peptide may used effectively to treat a variety of inflammatory and non-inflammatory disorders associated with aberrant β adrenergic signaling.

References Cited

1. Abebe W, Mustafa S J. A1 adenosine receptor-mediated Ins(1,4,5)P3 generation in allergic rabbit airway smooth muscle. Am. J. Physiol. 275: L990-L997, 1998.
2. Bai T R. Abnormalities in airway smooth muscle in fatal asthma. Am. Rev. Respir. Dis. 141:552-557, 1990.
3. Bai T R, Mak J C, Barnes, P J. A comparison of beta-adrenergic receptors and in vitro relaxant responses to isoproterenol in asthmatic airway smooth muscle. Am. J. Respir. Cell Mol. Biol. 6: 647-651, 1992.
4. Beasley R, Pearce N, Crane J, Burgess C. Beta-agonists: what is the evidence that their use increases the risk of asthma morbidity and mortality? J. Allergy Clin. Immunol. 103 (Suppl.):S18-S30, 1999.
5. Billington C K, Le Jeune I R, Young K W, Hall, I P. A major functional role for phosphodiesterase 4D5 in human airway smooth muscle cells. Am. J. Respir. Cell Mol. Biol. 38: 1-7, 2008.
6. Bousquet-Melou A, Galitzky J, Moreno C M, Berlan M, Lafontan M. Desensitization of b-adrenergic responses in adipocytes involves receptor subtypes and cAMP phosphodiesterase. Eur J Pharmacol. 289: 235-247, 1995.
7. Carozzi A, Camps M, Gierschik P, Parker P. Activation of phosphatidylinositol lipid-specific phospholipase beta 3 by G-protein beta-gamma subunits. FEBS Lett. 315: 340-342, 1993.
8. Chapman R W, House A, Jones H, Richard J, Celly C, Prelusky D, Ting P, Hunter J C, Lamca J, Phillips J E. Effect of inhaled roflumilast on the prevention and resolution of allergen-induced late phase airflow obstruction in Brown Norway rats. Eur. J. Pharmacol. 571: 215-221, 2007.
9. Conti M, Richter W, Mehats C, Livera G, Park J Y, Jin C. Cyclic AMP-specific PDE4 phosphodiesterases as critical components of cyclic AMP signaling. J. Biol. Chem. 278: 5493-5496, 2003.
10. Crespo P, et al. Ras-dependent activation of MAP kinase pathway mediated by G-protein beta gamma subunits. Nature 369: 418-420, 1994.
11. Daaka Y, Luttrell L M, Lefkowitz R J. Switching of the coupling of the β2-adrenergic receptor to different G proteins by protein kinase A. Nature. 390: 88-91, 1997.
12. Giembycz M A, Newton R. Beyond the dogma: novel β2-adrenoceptor signaling in the airways. Eur. Respir. J. 27:1286-1306, 2006.
13. Goldie R G, Spina D, Henry P J, Lulich K M, Paterson J W. In vitro responsiveness of human asthmatic bronchus to carbachol, histamine, β-adrenoceptor agonists and theophylline. Br. J. Clin. Pharmacol. 22: 669-676, 1986.
14. Grunstein M M, Veler H, Shan X, Larson J, Grunstein J S, Chuang S. Pro-Asthmatic effects and mechanisms of action of the dust mite allergen, Der p 1, in airway smooth muscle. J. Allergy Clin. Immunol. 116: 94-101, 2005.
15. Guo M, Pascual R M, Wang S, Fontana M F, Valancius C A, Panettieri R A Jr, Tilley S L, Penn R B. Cytokines regulate β-2-adrenergic receptor responsiveness in airway smooth muscle via multiple PKA- and EP2 receptor-dependent mechanisms. Biochemistry. 44: 13771-13782, 2005.
16. Hakonarson H, Herrick D J, Grunstein M M. Mechanism of impaired beta-adrenoceptor responsiveness in atopic sensitized airway smooth muscle. Am. J. Physiol. 269: L645-L652, 1995.
17. Hakonarson H, Herrick D J, Serrano P G, Grunstein M M. Mechanism of cytokine induced modulation of β-adrenoceptor responsiveness in airway smooth muscle. J. Clin. Invest. 97: 2593-2600, 1996.
18. Hakonarson H, Grunstein M. M. Regulation of second messengers associated with airway smooth muscle contraction and relaxation. Am. J Respir. Crit. Care Med. 158: S115-S122, 1998.

19. Hakonarson H, Maskeri N, Carter C, Hodinka R L, Campbell D, Grunstein M M. Mechanism of rhinovirus-induced changes in airway smooth muscle responsiveness. *J. Clin. Invest.* 102:1732-1741, 1998.
20. Hakonarson H, Grunstein M M. Autocrine regulation of airway smooth muscle responsiveness. *Respir. Physiol. Neurobiol.* 137: 263-276, 2003.
21. Hansen G, Jin S, Umetsu D T, Conti, M. Absence of muscarinic cholinergic airway responses in mice deficient in the cyclic nucleotide phosphodiesterase PDE4D. *Proc. Natl. Acad. Sci. USA.* 97: 6751-6756, 2000.
22. Houslay M D, Adams D R. PDE4 cAMP phosphodiesterases: modular enzymes that orchestrate signaling cross-talk, desensitization and compartmentalization. *Biochem J* 370:1-18, 2003.
23. Ichiki T. Role of cAMP response element binding protein in cardiovascular remodeling: good, bad, or both? *Arterioscler. Thromb. Vasc. Biol.* 26: 449-455, 2006.
24. Kanehiro A, Ikemura T, Makela M J, Lahn M, Joetham A, Dakhama A, Gelfand E W. Inhibition of phosphodiesterase 4 attenuates airway hyperresponsiveness and airway inflammation in a model of secondary allergen challenge. *Am. J. Respir. Crit. Care Med.* 163: 173-184, 2001.
25. Koch W J, Hawes B E, Allen L F, Lefkowitz R J. Direct evidence that Gi-coupled receptor stimulation of mitogen-activated protein kinase is mediated by Gβγ activation of p21ras. *Proc. Natl. Acad. Sci. USA.* 91: 12706-12710, 1994.
26. Koch W J, Hawes B E, Inglese J, Luttrell L M, Lefkowitz R J. Cellular expression of the carboxyl terminus of a G protein-coupled receptor kinase attenuates G beta gamma-mediated signaling. *J. Biol. Chem.* 269: 6193-61497, 1994.
27. Kogut M H, Genovese K J, He H. Flagellin and lipopolysaccharide stimulate the MEK-ERK signaling pathway in chicken heterophils through differential activation of the small GTPases, Ras and Rap1. *Mol. Immunol.* 44: 1729-1736, 2007.
28. Laporte J D, Moore P E, Abraham J H, Maksym G N, Fabry B, Panettieri R A Jr, Shore S. Role of ERK MAP kinases in responses of cultured human airway smooth muscle cells to IL-1β. *Am. J. Physiol.* 277, L943-L951, 1999.
29. Lefkowitz R J, Pierce K L, Luttrell L M. Dancing with different partners: protein kinase a phosphorylation of seven membrane-spanning receptors regulates their G protein-coupling specificity. *Mol. Pharmacol.* 62: 971-974, 2002.
30. Le Jeune I R, Shepherd M, Van Heeke G, Houslay M D, Hall I P. Cyclic AMP-dependent transcriptional up-regulation of phosphodiesterase 4D5 in human airway smooth muscle cells. Identification and characterization of a novel PDE4D5 promoter. *J. Biol. Chem.* 277: 35980-35989, 2002.
31. Lipworth B J. Airway subsensitivity with long-acting β2-agonists. Is there cause for concern? *Drug Saf* 16: 295-308, 1997.
32. Liu H, Palmer D, Jimmo S L, Tilley D G, Dunkerley H A, Pang S C, Maurice D H. Expression of phosphodiesterase 4D (PDE4D) is regulated by both the cyclic AMP-dependent protein kinase and mitogen-activated protein kinase signaling pathways. A potential mechanism allowing for the coordinated regulation of PDE4D activity and expression in cells. *J. Biol. Chem.* 275: 26615-26624, 2000.
33. Mehats C, Jin S L, Wahlstrom J, Law E. Umetsu D T, Conti M. PDE4D plays a critical role in the control of airway smooth muscle contraction. *FASEB J.* 17: 1831-1841, 2003.
34. McGraw D W, Elwing J M, Fogel K M, Wang W C, Glinka C B, Mihlbachler K A, Rothenberg M E, Liggett S B. Crosstalk between Gi and Gq/Gs pathways in airway smooth muscle regulates bronchial contractility and relaxation. *J. Clin. Invest.* 117: 1391-1398, 2007.
35. Penn R B, Panettieri R A Jr, Benovic J L. Mechanisms of acute desensitization of the β2AR-adenylyl cyclase pathway in human airway smooth muscle. *Am. J. Respir. Cell Mol. Biol.* 19: 338-348, 1998.
36. Sayers I, Swan C, Hall I P. The effect of beta2-adrenoceptor agonists on phospholipase C (beta1) signalling in human airway smooth muscle cells. *Eur. J. Pharmacol.* 531: 9-12, 2006.
37. Sears M R. Role of β-agonists in asthma fatalities. In Fatal asthma. A. L. Sheffer, editor. Marcel Dekker Inc. New York, N.Y., USA. 457-481, 1998.
38. Shan X, Hu A, Veler H, Fatma S, Grunstein J S, Chuang S, Grunstein M M. Regulation of toll-like receptor 4-induced pro-asthmatic changes in airway smooth muscle function by opposing actions of ERK1/2 and p38 MAPK signaling. *Am. J. Physiol.* 291: L324-L333, 2006.
39. Shore S A, Moore P E. Regulation of β-adrenergic responses in airway smooth muscle *Respir. Physiol. Neurobiol.* 137: 179-195, 2003.
40. Stork P J, Schmitt J M. Crosstalk between cAMP and MAP kinase signaling in the regulation of cell proliferation. *Trends Cell Biol.* 12: 258-266, 2002.
41. Sun J G, Deng Y M, Wu X, Tang H F, Deng J F, Chen J Q, Yang S Y, Xie Q. Inhibition of phosphodiesterase activity, airway inflammation and hyperresponsiveness by PDE4 inhibitor and glucocorticoid in a murine model of allergic asthma. *Life Sci.* 79:2077-2085, 2006.
42. Torphy T J, Zhou H L, Foley J J, Sarau H M, Manning C D, Barnette M S. Salbutamol up-regulates PDE4 activity and induces a heterologous desensitization of U937 cells to prostaglandin E2. Implications for the therapeutic use of β-adrenoceptor agonists. *J Biol Chem.* 270: 23598-23604, 1995.
43. van Schalkwyk E, Strydom K, Williams Z, Venter L, Leichtl S, Schmid-Wirlitsch C, Bredenbroker D, Bardin P G. Roflumilast, an oral, once-daily phosphodiesterase 4 inhibitor, attenuates allergen-induced asthmatic reactions. *J. Allergy Clin. Immunol.* 116: 292-298, 2005.
44. Willoughby D, Wong W, Schaack J, Scott J D, Cooper D M. An anchored PKA and PDE4 complex regulates subplasmalemmal cAMP dynamics. *EMBO J.* 25: 2051-2061, 2006.
45. Willoughby D, Baillie G S, Lynch M J, Ciruela A, Houslay M D, Cooper D M. Dynamic regulation, desensitization, and cross-talk in discrete subcellular microdomains during β2-adrenoceptor and prostanoid receptor cAMP signaling. *J Biol Chem.* 282: 34235-34249, 2007.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for the treatment of asthma in a patient in need thereof, comprising administration of an effective amount of an inhibitor of G βγ signaling, said administration being effective to reduce bronchoconstriction in said patient, wherein said inhibitor of G βγ signaling is a membrane permeable G βγ blocking peptide comprising SEQ ID NO: 1.

2. The method of claim 1, wherein asthma in said patient is exacerbated by long term use of β2-adrenergic receptor agonists.

3. The method of claim 1 wherein said inhibitor of G βγ signaling is delivered to a patient by a method selected from the group consisting of systemic, oral, intravenous, intramuscular, subcutaneous, intraorbital, intranasal, intracapsular, intraperitoneal, intracisternal, intratracheal, intraarticular administration, and absorption through the skin.

4. The method of claim 1, wherein said inhibitor of G βγ signaling is formulated for aerosol delivery and is delivered via inhalation.

5. The method of claim 4, wherein said aerosolized formulation comprises a propellant selected from the group consisting of halocarbons, hydrocarbons and esters.

6. The method of claim 1, further comprising administration of at least one anti-inflammatory agent selected from the group consisting of corticosteroids, sodium cromolyn, IgE inhibitors, phosphodiesterase inhibitors, methylxanthines, beta-adrenergic agents, and leukotriene modifiers.

7. The method of claim 6, wherein said anti-inflammatory agent is delivered simultaneously with said inhibitor of G βγ signaling.

8. The method of claim 6, wherein said anti-inflammatory agent is delivered sequentially, before or after delivery of said inhibitor of G βγ signaling.

* * * * *